United States Patent
DeBoer et al.

(10) Patent No.: US 7,141,859 B2
(45) Date of Patent: Nov. 28, 2006

(54) POROUS GAS SENSORS AND METHOD OF PREPARATION THEREOF

(75) Inventors: John DeBoer, Decatur, GA (US); Stephen Edward Lewis, Atlanta, GA (US); Peter Hesketh, Atlanta, GA (US); James Gole, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 11/094,584

(22) Filed: Mar. 30, 2005

(65) Prior Publication Data

US 2005/0193800 A1 Sep. 8, 2005

Related U.S. Application Data

(60) Continuation-in-part of application No. 11/041,358, filed on Jan. 24, 2005, which is a continuation of application No. 10/633,259, filed on Aug. 1, 2003, now Pat. No. 6,893,892, which is a division of application No. 10/268,860, filed on Oct. 10, 2002, now Pat. No. 6,673,644, which is a continuation-in-part of application No. 09/820,412, filed on Mar. 29, 2001, now Pat. No. 6,589,883.

(60) Provisional application No. 60/644,716, filed on Jan. 18, 2005, provisional application No. 60/563,674, filed on Apr. 20, 2004, provisional application No. 60/558,759, filed on Apr. 1, 2004.

(51) Int. Cl.
*H01L 27/14* (2006.01)
(52) U.S. Cl. .................. 257/414; 257/427; 257/423
(58) Field of Classification Search ................ 257/414
See application file for complete search history.

(56) References Cited

U.S. PATENT DOCUMENTS

| | | | |
|---|---|---|---|
| 4,294,891 A | 10/1981 | Yao et al. | 429/2 |
| 5,004,424 A | 4/1991 | Larminie | 434/301 |
| 5,074,987 A | 12/1991 | Thompson | 204/410 |
| 5,641,585 A | 6/1997 | Lessing et al. | 429/26 |
| 5,759,712 A | 6/1998 | Hockaday | 429/30 |
| 6,062,210 A | 5/2000 | Welles | 126/208 |
| 6,123,828 A | 9/2000 | Williams et al. | 205/787 |
| 6,289,888 B1 | 9/2001 | Welles | 126/263.01 |
| 6,312,846 B1 | 11/2001 | Marsh | 429/30 |
| 6,342,071 B1 | 1/2002 | Pless | 623/3.1 |
| 6,491,391 B1 | 12/2002 | Blum et al. | 351/159 |
| 6,517,203 B1 | 2/2003 | Blum et al. | 351/168 |
| 6,527,943 B1 | 3/2003 | Zhang et al. | 205/787 |
| 6,619,799 B1 | 9/2003 | Blum et al. | 351/168 |
| 6,627,964 B1 * | 9/2003 | Nakashima et al. | 257/414 |
| 6,906,392 B1 * | 6/2005 | Benzel et al. | 257/414 |
| 7,013,708 B1 * | 3/2006 | Cho et al. | 73/31.05 |
| 2002/0122972 A1 | 9/2002 | Klitsner et al. | |
| 2003/0082431 A1 | 5/2003 | Klitsner et al. | |

(Continued)

OTHER PUBLICATIONS

Gole, DeVincentis, and Seals; Chloride salt enhancement and stabilization of the photoluminescence from a porous silicon surface; Feb. 15, 2000; Physical Review B; pp. 5615-5631.

(Continued)

*Primary Examiner*—Thao P. Le
(74) *Attorney, Agent, or Firm*—Thomas, Kayden, Horstemeyer & Risley, LLP

(57) ABSTRACT

Devices including conductometric porous silicon gas sensors, methods of fabricating conductometric porous silicon gas sensors, methods of selecting a device, methods of detecting a concentration of a gas, and methods of analyzing data.

29 Claims, 13 Drawing Sheets

U.S. PATENT DOCUMENTS

2003/0138685 A1    7/2003    Jankowski et al.
2003/0170515 A1    9/2003    Wang et al.
2003/0170520 A1    9/2003    Fujii et al.

OTHER PUBLICATIONS

Prokes, Carlos, Seals and Gole; Defect study of light-emitting HCl-treated porous silicon; Jul. 15, 2000; Physical Review B; pp. 1878-1882.

Gole, Seals and Lillehei; Patterned metallization for porous silicon from electroless solution for direct electrical contact; 2000; Journal of the Electrochemical Society; pp. S-5-27-S-5-31.

Gole, DeVincentis and Seals; Optical pumping of dye-complexed and sensitized porous silicon increasing photoluminescence emission rates; 1999; The Journal of Physical Chemistry B; pp. 979-987.

Propst and Kohl; The Electrochemical Oxidation for Silicon and Formation of Porous Silicon in Acetonitrile; Apr. 1994; J. Electrochem. Soc.; pp. 1006-1013.

Prokes; Surface and optical properties of porous silicon; Feb. 1996; J. Mater. Res.; pp. 305-320.

Collins, Fauchet and Tischler; Porous silicon; From luminescence to LEDS; Jan. 1997; Physics Today; pp. 24-31.

Cullis, Canham and Calcott; The structural and luminescence properties of porous silicon; 1997; Applied Physics Reviews; pp. 909-965.

Kanemitsu; Light emission from porous silicon and related materials; 1995; Physics Reports; pp. 1-91.

Canham; Silicon quantum wire array fabrication by electrochemical and chemical dissolution of wafers; Sep. 1990; Appl. Phys. Letter; pp. 1046-1048.

John and Singh; Porous silicon: Theoretical studies; 1995; Physics Reports; pp. 93-151.

Koch, Petrova-Koch, Nikolov and Gavrilenko; Some perspectives on the luminescence mechanism via surface-confined states of porous Si; 1993; Mat. Res. Soc.; pp. 197-202.

Koch, Petrova-Koch and Muschik; The luminescence of porous Si: the case for the surface state mechanism; 1993; Journal of Luminescence; pp. 271-281.

Koch; Models and mechanisms for the luminescence of porous Si; 1993; Mat. Res. Soc.; pp. 319-329.

Gole and Dixon; Transformation, green to orange-red, of a porous silicon photoluminescent surface in solution; 1998; The Journal of Physical Chemistry B; pp. 33-39.

Gole and Dixon; Electrochemical methoxylation of an HF-etched porous silicon surface; 1998; The Journal of Physical Chemistry B; pp. 1768-1774.

Gole, Dudel and Seals; On the correlation of aqueous and nonaqueous in situ and ex situ photoluminescent emissions from porous silicon; 1998; J. Electrochem. Soc.; pp. 3284-3300.

Dudel and Gole; Stabilization of the photoluminescence from porous silicon: the competition between photoluminescence and dissolution; 1997; J. Appl. Phys.; pp. 402-406.

Seals, Dudel, Grantier and Gole; Trends in the interaction for the strong acids HCl, HBr, and HI with a photoluminescing porous silicon surface; 1997; The Journal of Physical Chemistry B; pp. 8860-8864.

Warntjes, Vieillard, Ozanam and Chazalviel; Electrochemical methozylation of porous silicon surface; Dec. 1995; J. Electrochem. Soc., pp. 4138-4142.

Gole, Dudel, Grantier and Dixon; Origin of porous silicon photoluminescence: Evidence for a surface bound oxyhydride-like emitter; Jul. 15, 1997; Physical Review B; pp. 2137-2153.

Dubin, Ozanam and Chazalviel; In situ luminescence and IR study of porous silicon during and after anodic oxidation; 1995; Thin Solid Films; pp. 87-91.

Koch and Kux; Prospects for infrared electroluminescence from porous silicon; 1993; Mat. Res. Soc.; pp. 391-396.

Fuchs, Rosenbauer, Brandt, Ernst, Finkbeiner, Stutzmann, Syassen, Weber, Queisser and Cardona; Visible luminescence from porous silicon and siloxene: recent results; 1993; Mat. Res. Soc.; pp. 203-208.

Lenward Seals, James L. Gole, Laam Angela Tse and Peter J. Hesketh; Rapid, Reversible, Sensitive Porous Silicon Gas Sensor; Journal of Applied Physics; Feb. 15, 2002; pp. 2519-2523.

* cited by examiner

POROUS GAS SENSORS AND METHOD OF PREPARATION THEREOF

CROSS-REFERENCE TO RELATED APPLICATION

This application is a continuation-in-part application, which claims priority to copending U.S. Utility Application entitled, "POROUS GAS SENSOR AND METHOD OF PREPARATION THEREOF," having Ser. No. 11/041,358, filed Jan. 24, 2005, which is a continuation of and claims priority to U.S. Utility Application entitled, "POROUS GAS SENSOR AND METHOD OF PREPARATION THEREOF," having Ser. No. 10/633,259, filed Aug. 1, 2003, now U.S. Pat. No. 6,893,892 which is a divisional application of U.S. Pat. No. 6,673,644 for "POROUS GAS SENSORS AND METHOD OF PREPARATION THEREOF" (formerly U.S. Utility Application having Ser. No. 10/268,860, filed on Oct. 10, 2002) now U.S. Pat. No. 6,673,644, which is a continuation-in-part of U.S. Pat. No. 6,589,883 for "ENHANCEMENT, STABILIZATION AND METALLIZATION OF POROUS SILICON" (formerly U.S. Utility Application having Ser. No. 09/820,412, filed Mar. 29, 2001), now U.S. Pat. No. 6,589,883 all of which are incorporated herein by reference.

This application claims priority to copending U.S. Provisional Applications entitled "GAS SENSORS" having Ser. No. 60/644,716, filed on Jan. 18, 2005; "PARAMETRIC METHOD FOR SIGNAL EXTRACTION FROM CHEMICAL SENSOR RESPONSE" having Ser. No. 60/558,759, filed on Apr. 1, 2004; and "SENSITIVITY AND SELECTIVITY ENHANCEMENT FOR POROUS SILICON GAS SENSORS THROUGH ELECTROLESS METALLIZATION" having Ser. No. 60/563,674, filed on Apr. 20, 2004, all of which are incorporated herein by reference.

TECHNICAL FIELD

The present disclosure is generally related to porous silicon substrates and, more particularly, is related to porous silicon sensors and methods of preparation thereof.

BACKGROUND

Gas sensors are multifarious in modern industry. For each application, a different sensor configuration is usually needed to meet the criteria of a particular application. An arrayed device, capable of being inexpensively calibrated for a prescribed set of analyte gases, would present an ideal device for a diversity of applications. At a recent NSF/NIST "Process Measurement and Control Workshop" several critical challenges for further sensor development were identified. For instance, individual sensor systems should be produced cost effectively in any scale processes. Also, government and industry standards require the operation of a device in a safely monitored and environmentally friendly manner. Key to developing these new capabilities is the need for easier calibration models, methods to transfer calibration sensors with given performance properties and/or process parameters, calibration transfer among multiple 'like' sensors, and transitioning from laboratory development to plant operation.

Thus, a heretofore unaddressed need exists in the industry for sensors that address one or more of the aforementioned deficiencies and inadequacies.

SUMMARY

Devices including conductometric porous silicon gas sensors, methods of fabricating conductometric porous silicon gas sensors, methods of selecting a device, and methods of analyzing data, are disclosed.

A representative device, among others, includes a conductometric porous silicon gas sensor, a first contact, and a second contact. The conductometric porous silicon gas sensor includes a monolithic silicon substrate having a porous silicon layer and a protective layer. The first contact disposed on a first portion of the porous silicon layer and a first portion of the protective layer. The second contact disposed on a second portion of the porous silicon layer and a second portion of the protective layer. The conductometric porous silicon gas sensor is operative to transduce the presence of a gas into an impedance change across the first contact and the second contact, wherein the impedance change correlates to the gas concentration.

Another representative device, among others, includes a conductometric porous silicon gas sensor. The conductometric porous silicon gas sensor includes a monolithic silicon substrate having a porous silicon layer and a protective layer. The protective layer is disposed on top of the silicon substrate and adjacent to the porous silicon layer. The protective layer can include a silicon carbide layer, a silicon nitride layer, a polymer layer, a silicon oxynitride layer, an insulating dielectric film, a ceramic layer, a photoresist layer, a polyimide layer, and/or combinations thereof. The porous silicon layer has a first portion and a second portion that are not contiguous. The protective layer has a first portion and a second portion that are not contiguous. The first portion of the protective layer is contiguous with the first portion of the porous silicon layer. The second portion of the protective layer is contiguous with the second portion of the porous silicon layer. A first metal layer is disposed on the first portion of the porous silicon layer and the first portion of the protective layer to form a first contact. A second metal layer is disposed on the second portion of the porous silicon layer and the second portion of the protective layer to a form second contact. The conductometric porous silicon gas sensor is operative to transduce the presence of a gas into an impedance change across the first contact and the second contact. The impedance change correlates to the gas concentration.

Another embodiment provides for a method, among others, for fabricating a sensor. The method includes: providing a silicon substrate having a protective layer disposed on a first portion of the silicon substrate; converting a first area of the silicon substrate into a porous silicon layer, wherein the first area does not have the protective layer disposed thereon; forming a first contact onto a first portion of the porous silicon layer and onto a first portion of the protective layer, wherein the first portion of the protective layer is contiguous with the first portion of the porous silicon layer; and forming a second contact onto a second portion of the porous silicon layer and onto a second portion of the protective layer, wherein the second portion of the protective layer is contiguous with the second portion of the porous silicon layer, and wherein a third portion of the porous silicon layer is between the first portion and the second portion of the porous silicon layer.

Another embodiment provides for a method, among others, for fabricating a sensor. The method includes: providing a silicon substrate having a porous silicon region that is disposed between a first substrate region and a second substrate region, wherein the first substrate region and the second substrate region have a protective layer disposed thereon; disposing a shadow mask on the porous silicon layer and the protective layer, wherein the shadow mask exposes a first portion of the porous silicon layer and a first portion of the protective layer, and exposes a second portion of the porous silicon layer and a second portion of the protective layer; disposing a first contact onto the first portion of the porous silicon layer and onto the first portion of the first protective layer; and disposing a second contact onto the second portion of the porous silicon layer and onto the second portion of the second protective layer, and wherein a third portion of the porous silicon layer is between the first portion and the second portion of the porous silicon layer.

Another embodiment provides for a method, among others, of selecting a device. The method includes: providing a sensor; introducing a gas stream to the sensor; measuring an impedance change in the sensor; and validating the sensor.

Another embodiment provides for a method, among others, of detecting a concentration of a gas. The method includes: providing the sensor; introducing the gas to the sensor; measuring an impedance change in the sensor; and correlating the impedance change to the concentration of the gas.

Another embodiment provides for a method, among others, of analyzing data. The method includes: receiving a signal comprising a measured impedance change of a device; and characterizing the performance of the device based on the measured impedance change.

Other systems, methods, features, and advantages of the present disclosure will be or become apparent to one with skill in the art upon examination of the following detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is a top view of a representative embodiment of the porous silicon sensor of the present disclosure, while

FIG. 2A is a top view of a representative embodiment of another porous silicon sensor of the present disclosure, while

DETAILED DESCRIPTION

Figure 1A:
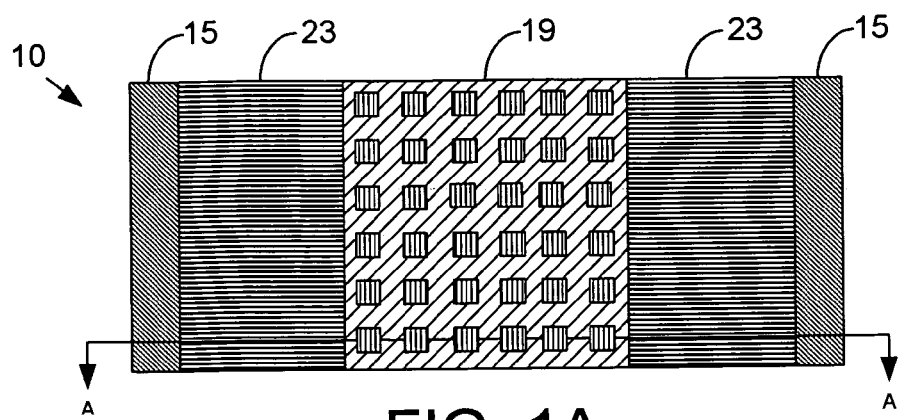

1. Stabilization and Enhancement of Porous Silicon

One of a number of embodiments of the present disclosure includes the treatment of PS substrates generated in an aqueous and nonaqueous etch with an HCl(H$_2$O) solution, which results in the stabilization and enhancement of the in situ PL of the PS substrates. More specifically, in an exemplary embodiment, in a post-etch treatment method, an HCl(H$_2$O) solution can be used to enhance and stabilize the PL (in situ) from a PS substrate. In addition, in an other exemplary embodiment, a method of treating the PS substrate with HCl(H$_2$O) followed by an alcohol solution (e.g. methanol or ethanol) further enhances and stabilizes the PL (in situ and ex situ) of the substrate. A non-limiting illustrative example includes PS substrates that are treated in an aqueous hydrochloric acid and water (HCl/H$_2$O) solution and display a strongly enhanced in-situ luminescence; however, the PL decays rapidly in an ex-situ environment without treatment in alcohol, preferably a high purity alcohol such as methanol. An exemplary embodiment includes treating the PS with methanol (MeOH). Further, PS substrates treated in an HCl (H$_2$O)/alcohol solution (of at least 0.2 molar (M) maintain their enhancement for extended periods of time. The PS substrate may be stabilized and enhanced by the presence of a chloride ion (Cl$^-$). The treatment appears to be independent of the method of preparing the PS substrate, implying that the chloride salt treatment largely stabilizes the surface states of the photoluminescent PS substrate. This stabilization may be demonstrated by various techniques including, but not limited to the following: scanning electron micrographs (SEM), which show the profound change which accompanies the HCl treatment of the PS surface; Energy Dispersive Spectroscopy (EDS) which, reveals chloride incorporation into the PS surface at strongly photoluminescent regions; and Raman scattering, which demonstrates that the PL is correlated with the creation of amorphous structural regions. All of these testing methods indicate the manner in which the chloride salt stabilizes the PS substrate.

2. Enhancement of the PS Photoluminescence Using Dyes

Another exemplary embodiment of the present disclosure includes treating PS substrates with a dye (e.g., 3,3'-diethyloxadicarbocyanine iodide (DODCI) and Rhodamine 700). In general, the dye should have negligible absorption at the wavelengths of maximum absorption for the PS substrate. After a period of aging in darkness these dye-treated PS substrates can be pumped at about 337.1 nanometers (nm) (nitrogen laser) near the maximum in the PS absorption spectrum (far from the major absorption regions of the impregnating dye). Time-dependent PL histograms indicate that the resulting PL emission rate is enhanced. The enhancement in the PL emission rate may be attributed to an interaction between the surface-bound fluorophors, which characterize PS substrates and the dye. This interaction results in the creation of a distribution of PS-dye complexes, which enhance the nominal PL emission rate from the untreated PS surface. In a preferred embodiment, the DODCI$^-$ treated samples display PL that exceeds that of nominally prepared PS by a factor of five or more.

3. Metallization of PS

A further exemplary embodiment of the present disclosure includes the metallization of a PS substrate. One of the existing challenges in fabricating PS devices rests with establishing electrical contact to the PS substrate. In an exemplary embodiment, PS substrates are capable of being metallized in a controlled manner using electroless metal-coating solutions and inducing the metal to plate onto the PS substrate in regions which are PL. An exemplary embodiment includes using an electroless metal solution, which can be introduced to the PS substrate after treating the PS substrate with a hydrazine solution so that subsequently the metal can be deposited onto the PS substrate in a controlled manner. The metal-containing solution includes, but is not limited to, any one, or all, or combination of copper, silver, gold, and other metals that are commonly deposited using electroless techniques. This method is capable of using the "long-lived" PS substrate PL to enhance reduction at the PS substrate surface. This may be accomplished by creating excited fluorophors on the PS surface to enhance interaction and reduction at the PS substrate surface. Using this method enables metals to readily deposit onto the PS substrate within PS micropores and nanopores. Further, under controlled conditions the metallization only occurs where the PS surface is illuminated with light from a light source. (e.g. Xenon (Xe) arc lamp, Helium-Neon (HeNe) laser, or other appropriate light source). Furthermore, the thickness of the metallization deposit is proportional to the time and intensity of exposure of the PS surface to the light source.

In conventional electroless metal plating, the surface is usually first coated with palladium (Pd) metal to catalyze the deposition process. For purposes of this disclosure, the addition of a catalyst to the metal plating process is considered to be operating under catalytic conditions. However, embodiments of the present disclosure do not require an additional catalyst, which, for purposes of this disclosure, means that the method is performed under "non-catalytic conditions." Indeed, in the method of the present disclosure, the illuminated PS surface itself is catalyzing the deposition. Further, localized heating is not promoting the deposition; rather the metal deposition occurs when the PS substrate is illuminated at wavelengths less than about 750 nm, consistent with its bandgap.

A further exemplary embodiment of the present disclosure includes the metallization of a PS substrate to produce a low electrical resistance metallized PS substrate that has a resistance from about 20 ohms to about 1000 ohms. Another embodiment includes metallized PS substrates with resistances between about 20 ohms and about 100 ohms. Still a further embodiment includes metallizated PS substrates with resistances between about 20 ohms and about 60 ohms.

4. Porous Silicon Sensor

A further exemplary embodiment of the present disclosure includes a porous silicon (PS) sensor. The PS sensor includes a silicon substrate, a PS layer on a portion of the silicon substrate, and a front contact disposed onto a portion of the PS region. The PS region can include a nanoporous or a macroporous and nanoporous hybrid framework. In the preferred embodiment, the front contact can be disposed within the macroporous and nanoporous hybrid framework. The front contact can include one or more front contact portions made of metals such as, for example, copper, silver, and gold.

The PS sensor can be used to detect gases or liquids. In particular, PS gas sensors, in accordance with the present disclosure, have a rapid and reversible response to analyte gases at room temperature. The PS sensor has a contact resistance between the front contact and the PS between about 10 and 100 ohms, 20 to 100 ohms, and preferably about 20 and 60 ohms. In addition, the PS sensor has a resistivity between about 0.01 ohms cm to 10 ohms/cm$^2$, and preferably about 0.1 ohms cm to 1 ohms cm. Further, the PS sensor operates at a bias voltage of between about 1 and 20 millivolts, and preferably about 1 to 10 millivolts. The PS sensors have a sensitivity of at least as low as 10 parts per million (ppm).

1. Stabilization and Enhancement of Porous Silicon $HCl(H_2O)$/Alcohol PL Enhancement of Porous Silicon Substrates As discussed above, an exemplary embodiment of the present disclosure includes a method and system of treating PS substrates with an $HCl/(H_2O)$ solution to enhance and stabilize the PL of the PS substrates. PS substrates treated in an $HCl/(H_2O)$ solution display a strongly enhanced in situ PL. PS substrates treated in an $HCl/(H_2O)$ alcohol solution (e.g. at least 0.2 M) display enhanced in situ and ex situ PL and can maintain enhancement for time periods on the order of years. Another exemplary embodiment includes treating the porous silicon substrates with an $HCl/(H_2O)$ solution (e.g. at least 0.2 M) then subsequently treating the PS substrates with an alcohol. This embodiment also enhances and stabilizes the in situ and ex situ PL of the PS substrate.

More specifically, the post-etch method of enhancing and stabilizing the PL of a PS substrate includes treating the PS substrate with an $HCl/(H_2O)$ solution. The PS substrate includes, but is not limited to a microporous framework upon which is superimposed a nanoporous layer. The $HCl/(H_2O)$ solution is at least 0.2 M. In one exemplary embodiment, the $HCl/(H_2O)$ solution includes an alcohol. Alcohols that can be used include, but are not limited to, ethanol, methanol, other appropriate alcohols for treating PS substrates, and combinations thereof. In another exemplary embodiment, the PS substrate is treated with the $HCl/(H_2O)$ solution, then subsequently treated with an alcohol (e.g., ethanol, methanol, etc.) This method of treatment enhances the in situ and enhances and stabilizes the ex situ PL.

Chloride-ion stabilization appears independent of the method of preparing the PS substrates, implying that the chloride salt treatment largely stabilizes the surface constituency of the photoluminescent PS substrate. This can be demonstrated by scanning electron micrographs, which show the change that accompanies the HCl treatment of the PS substrate surface. Further, energy dispersive spectroscopy reveals chloride incorporation into the PS surface at strongly PL regions. Furthermore, Raman scattering demonstrates that the PS substrate PL enhancement is correlated with the creation of amorphous structural regions. In conjunction with detailed quantum-chemical modeling, time-dependent histograms obtained for the HCl-treated systems indicate that the resulting PL, initiated through the optional pumping of the HCl-modified surface, displays the manifestation of a significant surface interaction. This interaction might result in the formation of both chlorosilanones and chlorsilylenes. In addition, the hydrogen cation ($H^+$) may play a role in the stabilization of the silanol-based features of the PS substrate surface both as a contribution to the flourophor formation and by decreasing the hydroxyl ($OH^-$) concentration in solution.

EXAMPLE 1

Preparation of PS

The following is a non-limiting illustrative example of an embodiment of the present disclosure that is described in more detail in Gole, et al., *Phys. Rev. B*, 61, 5615 (2000); Gole, et al., *J. Phys. Chem.* 101, 8864 (1997); Gole, et al. *Phys. Rev. B*, 62, 1878 (2000), which all are herein incorporated by reference. This example is not intended to limit the scope of any embodiment of the present disclosure, but rather is intended to provide specific experimental conditions and results. Therefore, one skilled in the art would understand that many experimental conditions can be modified, but it is intended that these modifications are within the scope of the various embodiments of this disclosure.

a. PS Preparation

Single crystal <100> boron doped silicon wafers with resistivities of about 50–100 ohm cm were used in the current study. Both highly branched nanoporous and hybrid nanoporous-covered microporous PS substrate samples were fabricated in an electrochemical cell constructed from high-density polyethylene. The working electrode was attached to the back of a p-type silicon wafer <100> (aluminum (Al) coated) and the counter electrode corresponded to a platinum (Pt) foil placed in solution. The cell was sealed to the front of the wafer, using a clamp, as about a 1 centimeter squared ($cm^2$) section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% hydrofluoric acid (HF) in methanol solution while the hybrid nanoporous-covered microporous samples were etched in a solution of 1 M $H_2O$, 1M HF, and 0.1M tetrabutylammonium perchlorate (TBAP), all in acetonitrile. The nanoporous etched samples were etched at a current density ranging from about 2 to 30 miliamp per centimeter squared ($mA/cm^2$) and preferably about 8 $mA/cm^2$ for about 50 to 75 minutes while the hybrid samples were etched with a current density of about 8 $mA/cm^2$, for between 50 and 75 min. Using this latter procedure, pores approximately 1 to 2 µm wide by about 10 µm deep were formed, and well covered by a coating of nanoporous silicon.

b. PS Preparation

Single-crystal <100>, boron-doped silicon wafers (substrate) of resistivity ranging from about 1 to about 50 ohm cm were also etched in an alternative aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode may be connected through a Teflon™ cap, which was tightly fitted to a cuvette containing the etch solution. Ohmic contacts were made to the wafer by connecting a wire to the thin film of aluminum using conductive paint. Etching currents ranged from about 2 to 30 $mA/cm^2$, but the samples considered here were usually etched at 8 $mA/cm^2$ for 10 minutes.

These aqueous HF-etching procedures are capable of leading to the formation of a "nanoporous" surface on the silicon wafer. However, in order to obtain a thicker nanoporous coating and increase the sampling volume, Si<100> samples were treated in a 25% HF in methanol solution at a current density of about 14 $mA/cm^2$ for a period of about 30 min. In all cases, the prepared aqueous samples were either treated directly in solution or washed in spectral quality methanol and dried in air. They were then subsequently transferred to a crucible containing either methanol or the post-etch chloride solution of interest.

Samples prepared in about 20% HF/MeOH aqueous etching solution, once rinsed in a combination of doubly deionized water and methanol or ethanol and allowed to dry, yield a significant ex situ photoluminescence. If a cleaned sample is immediately placed in double deionized water, a gradual rise in the in situ PL intensity at 620 nm can be observed. Similarly, if such a cleaned sample is placed in an ultra high purity low molecular weight alcohol (e.g. methanol and ethanol) solution, the in situ PL will slowly increase and gradually diminish on the time scale of several hours. However, it is to be noted that this behavior is in sharp contrast to the effect of the alcohols in combination with HF: this combination rapidly quenches the PL within several minutes.

c. PL Stabilization Using HCl Treatment

The post-etch treatment of the PS substrates with an aqueous HCl solution and the enhancement and stabilization is now discussed. A PS sample prepared by aqueous etch is first etched in a methanol/20% HF [6 mol/l HF in MeOH (aq)] solution for 10 min., washed with methanol, dried in air, and then placed first in a solution of doubly deionized water and then dilute 6M HCl. The intensity of the PL, excited by a nitrogen ($N_2$) laser, increases somewhat upon removal from the HF etch solution and again increases gradually as the sample is placed in water. However, upon adding HCl the orange-red PL intensity increases significantly and remains constant over the time period (up to about 3.5 h) in which the sample is present in the HCl solution. Within the time frame of these processes, the wavelength-dependent spectral profile of the PL emission spectrum appears to have been altered only slightly from the time it was removed from the HF etching solution and dried in air through the period in which the sample remained in the HCl solution. The introduction of a high concentration of HCl has stabilized the PS photoluminescence.

In contrast to the stabilizing effect that 6M hydrochloric acid has on the PS substrates surface, a 2.75M hydrogen iodide (HI) solution almost completely quenches the PL. The effect of a 4.5M hydrogen bromide (HBr) solution is intermediate. The effect of the HI solution can be attributed to the strong quenching of surface-bound flourophors resulting from the formation of $I_2$ and $I_3$ in an oxidizing acidic environment. A similar effect also occurs with bromine, albeit to a much lesser extent.

d. PL Stabilization Using NaCl Solution Treatment

Post-etch treatment of the PS substrate in a methanol-NaCl solution is now discussed. The pronounced stabilization of the PS substrate photoluminescence in the 6M HCl solution focuses on the effect that the chloride ion may have on the PL process. The introduction of an aqueous etched (20% HF/MeOH) PS substrate sample into a saturated NaCl/MeOH solution produces a clear saturating PL emission signal. This is manifest in two ways. In the absence of sodium chloride (NaCl), the 620-nm PL from the PS substrate placed in methanol solution slowly rises, eventually peaks, and then more gradually decreases in intensity. If NaCl is placed into this solution before the PL has reached its maximum intensity in methanol, the PL will slowly increase to a maximum then plateau. For the introduction of the PS substrate sample into a NaCl-saturated solution in methanol, this plateau is reached over a time scale of several hours (compared to about 30 min for a 6 M HCl solution). Furthermore, the photon-count level at the maximum PL intensity appears to be considerably muted relative to the observed maximum for a PS substrate sample in methanol alone. In contrast, if the saturated NaCl solution is introduced to the methanol solution after the PL photon-count level has peaked in the methanol solution, the PL is found to plateau at an intensity corresponding closely to that at the time of the NaCl introduction.

e. Treatment Using Tetrabutylammonium Chloride

Post-etch treatment of PS substrate samples in tetrabutylammonium chloride (TBAC) solution is now discussed. The results observed when placing a prepared PS substrate sample in 6M HCl and saturated NaCl solutions certainly call attention to the potential role of the chloride ion in stabilizing the PS substrate photoluminescence. In order to study the effect of varying chloride-ion concentrations on the PS substrate luminescence, both tetrabutylammonium perchloride (TBAC) and HCl solutions are, studied.

The PS substrates PL at 620 nm is monitored after a sample, etched in a 20% HF/MeOH solution, is washed in methanol, dried in air, and then placed in a tetrabutylammonium chloride (TBAC) in methanol solution. The TBAC concentrations used include 0.1M, 0.2M, 0.3M, 0.4M and 1.0M. These experiments can be used to compare directly to the NaCl/MeOH saturated solution results. The 0.1M TBAC solution leads to a PL intensity, which peaks at about 4300 counts, seventy five minutes into the bath cycle, and then monotonically decreases to about 1000 counts within 5 hours. The source of the PS luminescence is temporarily enhanced, but it is not being stabilized at longer time scales. When the chloride concentration is raised to 0.2M, the photon-count level increases moderately as the PL intensity peaks at about 4800 counts, now 150 min. into the bath cycle. The signal again monotonically decreases to about 1000 counts within 5 hours. This trend continues for the 0.3M solution as the PL intensity peaks at about 6500 counts, 240 min into the run; however, despite a significant peak photon count, an eventual drop-off the PL signal is observed. The 0.4M chloride-ion solution again demonstrates an increased photon-count level (peak about 12000 counts). There is also a notable decrease in the rate of PL decay. This trend appears to reverse for the 1M concentrated $Cl^{-1}$ solution. Although the PS luminescence peaks on a shorter time scale, the PL peak level has dropped to about 6000 counts and also decays at a much more rapid rate, clearly paralleling that for the 0.1M and 0.2M solutions. Thus, for the tetrabutylammonium counterion ($TBA^+$), evidence is produced for a peak effective chloride-ion concentration but no evidence is produced for an extended stabilization of the PL signal with time.

f. HCl Concentration Effect on PL

In situ stabilization in HCl solutions of varying concentrations is now discussed. The results obtained in saturated NaCl and TBAC solutions emphasize the remarkable PL stabilization that is inherent to a PS sample bathed by a 6 M HCl solution. Next, a comparison of various concentrations of HCl is conducted. The concentrations include 0.1M, 0.2M, 0.3M, 1M, 2M, and 3M. For a 3M HCl solution in either water or methanol, the photon count rate is comparable to that for the 6M HCl solution. The count rate is still rising after 6.5 h in dilute HCl, whereas it levels off at about 20000 counts in the 6M HCl/($H_2O$) MeOH solution after approximately 2 h. Both bath solutions demonstrate a profound stabilizing and enhancing effect on the PS emission intensity.

As the HCl molarity decreases, there are clear subtle changes in the in situ PL. For the 2M and 1M dilute HCl/($H_2O$) solutions, the count rate is again comparable to that for the higher molarities and still rising after 6 h; however, the count rate in the 2M HCl/MeOH solution has already dropped to about 14000 (although appearing reasonably stabilized) and shows an even sharper decline for the 1M solution where a maximum intensity of about 5000 counts occurs about 2 h into the time scan and a precipitous decrease to barely 3000 counts is observed at 6 h.

The HCl-water system displays a remarkable in situ enhancement and stabilization. With further dilution to 0.3M, one finds a that comparable but possibly a slightly increased enhancement of the PL intensity is observed, which is still rising to about 25,000 counts after 6 h of PS substrate sample exposure to the HCl solution. At 0.2M, the HCl solution again displays a comparable stabilization that appears to plateau at about 22000 counts. However, at 0.1M, the HCl solution induces a much smaller enhancement of the PL signal from a sample photoluminescing in doubly deionized water. Furthermore, the stabilization of the signal is marginal as shown by a peaking at about 2625 counts approximately 4 h into the run. The threshold for stabilization and enhancement thus appears quite dramatic.

The results shown for HCl suggest the importance of the $H^+$ counterion generated from the strong acid HCl as well as the chloride ion. The $H^+$-ion concentration may play a role in stabilizing silanol-based features on the PS substrate surface both as a contributor to flurophor formation and by decreasing the [$OH^-$] concentration in solution. This is supported because the introduction of NaOH into this bath solution completely quenches the PL as it significantly increases the hydroxyl-ion concentration.

Ex situ PL from HCl-treated PS substrates is now discussed. The samples that have been treated in HCl($H_2O$)/MeOH and HCl/$H_2O$ solutions exhibit distinctly different ex situ behavior. The following demonstrates the different behavior. The growth of the in situ PL emission in a 1M HCl ($H_2O$)/MeOH solution peaks at about 12500 counts. Upon removal from the HCl($H_2O$)/MeOH bath, the ex situ PL emission intensity continues to maintain itself for periods exceeding several months. A similar treatment of the PS substrate surface in 3 M HCl ($H_2O$)/MeOH also produces a highly photoluminescent ex situ sample with a considerably higher long-term photoluminescent emission intensity peaking at about 18000–20000 counts (about 620 nm). In sharp contrast, if a PS substrate sample treated in an HCl/$H_2O$ solution and characterized by a PL emission intensity close to 20000 counts is removed from the solution and dried in air, the PL emission intensity drops to about 4000 counts at 620 nm within 24 h even decreasing precipitously during the laser pumping and PL measurement period to about 3000 counts. Another comparison shows long-term PL stability, for a 1M HCl/$H_2O$-tested sample that is immediately placed in ultra high purity methanol. The PL scans display not only a long-term stability but also a peak intensity considerably redshifted (~500 Å). The ex situ PL signal from an HCl/$H_2O$ solution-treated sample is almost completely extinguished within only a few days. However, if the PS substrate sample is rinsed in ultra high purity methanol after an in situ HCl/$H_2O$ treatment and allowed to remain in a methanol solution for two to three days, the PL intensity can significantly be maintained, ex situ, indefinitely.

2. Dye Enhanced PL of PS Substrates

Room temperature PL of PS substrates has attracted considerable attention primarily because of its potential use in the development of silicon based optoelectronics, displays, and sensors. However, the relatively long excited state lifetime associated with this PL, which appears to be of the order of tens to hundreds of microseconds, is problematic for some of these applications. The efficiency and wavelength range of the emitted light can be affected by the physical and electronic structure of the surface, the nature of the etching solution, and the nature of the environment into which the etched sample is placed.

These outlined results suggest the possibility that several common fluorescent dyes, whose radiative lifetimes are of the order of nanoseconds, might be made to interact with the PS substrate surface so as to considerably improve the observed PL rate. Strong physisorption or chemisorption of certain of these fluorescent dyes with the fluorescent emitter on the PS substrate surface through complexation enhance the quantum yield and modify the lifetime of the fluorescent events associated with the PS substrate.

More specifically, the post-etch enhancement of the PL from a PS substrate, which has a microporous framework on which is superimposed a nanoporous layer, includes treating the PS substrate with a dye. The dyes that can be used include, but are not limited to, 3,3-diethyloxadicarbacyamine iodide, Rhodamine dye compounds (e.g. Rhodamine 6G, Rhodamine 700), Fluorocein, dicyanomethylene (DCM) dye compounds (e.g. 4-dicyanomethylene-2-methyl-6-(p-dioctylaminostyryl)-4H-pyran, 4-dicyanomethylene-2-methyl-6-(p-dimethylaminostyryl)-4H-pyran, 4-dicyanomethylene-2-methyl-6-[2-(1-methyl-1,2,3,4-tetrahydroquinolin-6-yl)ethenyl]-4H-pyran), 4-dicyanomethylene-2-methyl-6-[2-(2,3,6,7-tetrahydro-1H,5H-benzo[ij]quinolizin-8-yl)ethenyl]-4H-pyran), and other dyes that have negligible absorption at the wavelengths of maximum absorption for the PS substrate.

EXAMPLE 2

The following is a non-limiting illustrative example of an embodiment of the present disclosure and is described in more detail in Gole, et al., J. Phys, Chem. B, 103, 979 (1999), which is incorporated herein by reference. This example is not intended to limit the scope of any embodiment of the present disclosure, but rather is intended to provide specific experimental conditions and results. Therefore, one skilled in the art would understand that many experimental conditions can be modified, but it is intended that these modifications are within the scope of the embodiments of this disclosure.

As discussed for example 1 and 2, single crystal <100> boron doped silicon wafers with resistivities of about 50–100 ohm-cm were used in the current study. Both highly branched nanoporous and hybrid nanoporous covered microporous PS substrate samples were fabricated in an electrochemical cell constructed from high-density polyethylene. The working electrode was attached to the back of a p-type silicon wafer <100> (aluminum coated) and the counter electrode corresponded to a platinum foil placed in solution. The cell was sealed to the front of the wafer, using a clamp, as about a 1 $cm^2$ section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% HF in methanol solution while the hybrid samples were etched in a solution of 1 M $H_2O$, 1M HF, and 0.1M tetrabutylammonium percholate (TBAP), all in acetonitrile. The aqueous etched samples were etched at a current density ranging from about 2 to 30 mA/$cm^2$, and preferably about 8 mA/$cm^2$, for about 50 to 75 minutes while the hybrid samples were etched with a current density of about 8 mA/$cm^2$ for between 50 and 75 min. Using this latter procedure, pores approximately 1 to 2 μm wide by about 10 μm deep were formed, and well covered by a coating of nanoporous silicon.

Further, as discussed in example 1, single-crystal <100>, boron-doped silicon wafers (substrate) of resistivity ranging from about 1 to about 50 ohm cm were also etched in an aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode could be connected through a Teflon cap, which was tightly fitted to a cuvette containing the etch solution. Ohmic contacts were made to the wafer by connecting a wire to the thin film of aluminum using conductive paint. Etching currents ranged from about 2 to 30 mA/cm$^2$, but the samples considered here were usually etched at 8 mA/cm$^2$ for 10 minutes.

Prepared aqueous and hybrid samples were removed from the etching solution, washed in reagent grade methanol and treated with $10^{-3}$ molar (in doubly distilled $H_2O$) 3,3'-diethyloxadicarbocyanine iodide (DODCI) or Rhodamine 700. The PS substrate samples were dipped for several seconds or soaked for periods extending to about 45 minutes.

Pore structure and PL emission from PS substrates for untreated PS substrate samples is now discussed. The PL emission from aqueous and hybrid etched samples observed over the period 1.5–100 μs after excitation (PLE) at 337.1 nm (t=0) suggests that the PL observed for the hybrid etched sample exceeds that for the aqueous etched sample and demonstrates a slight 10–15 nm red shift.

PS substrates are known in the art to display a "green" PL resulting from an intermediate precursor state in the earlier stages of the emission process. The temporal decay and spectral profile of the "green" PL and transformation to a final "orange-red" PL emission during and following PS formation suggest the coupling of these PL emitters to the PS surface. The manifestations of the green and orange-red emission features in spectra are virtually identical for the aqueous and hybrid etched samples. Observed spectrum histograms represent the first clear observation of the "green" luminescence feature in an air-aged sample and demonstrate the magnitude of its contribution to the overall spectrum. With time (1) the "green" and "orange-red" emission features merge into each other as the source of the green emitter undergoes oxidative transformation to the final "orange-red" emitter, and (2) the longer wavelength features contributing initially to the orange-red emission are seen to decay most rapidly leading to what appears to be the manifestation of a blue shift in this feature in the absence of etching.

After 5.5 μs, for the aqueous etched sample, and 9.5 μs for the hybrid etched sample, the observed spectral features change little with delay time and the emission signal over the gate width of the scan begins to decrease. The dominant characteristics of the 1.5–100 μs spectra develop over the time span of the histograms, and with longer time delays, the monitored emission, while maintaining an identical wavelength dependence, decreases precipitously in intensity. The data demonstrate a nearly parallel although slightly different development of the PL intensity for the aqueous and hybrid etches and an overall spectral distribution which is quite similar for these etched samples.

Dye-treated PS substrates are now discussed. Dyes, such as DODCI and Rhodamine 700, have been used because of their negligible absorbance in the 350±20 nm range, the approximate peak absorption range of the PS excitation spectrum. The absorption spectrum for DODCI demonstrates a minimal absorbance for λ=330–470 nm. Rhodamine 700 is also a reasonable candidate although this dye does display a small absorbence at λ<330 nm.

Here, the focus is to create an environment for the energy transfer pumping of the adsorbed dye and/or the mediation of the longer-lived fluorescence from the PS substrate due to PS-dye complexation. As the optical pumping of the PS substrate surface is known to access a long-lived excited state triplet exciton, this excited state can be an energy reservoir for subsequent energy (or electron) transfer between the PS substrate surface and the adsorbed dye. Such transfer might take place through the pumping of a dye molecule in close proximity to the PS substrate surface via a fast intermolecular electron transfer. Alternatively, the dye chemisorbed with the surface-active exciton could receive the exciton energy via fast intramolecular energy transfer along a short bonding chain. Finally, the presence of this much more efficient radiator could enhance the PS substrate emission rate simply through complexation with the PS fluorophors.

Samples exposed to DODCI or Rhodamine 700 dye, when pumped at 337.1 nm by a nitrogen laser, display an initial quenching of the PS substrate PL followed by an expected slow and continued increase in the PL emission rate upon aging in the dark, in air, for an extended period. The aging cycle eventually produces a PL signal which has been maximized and maintained for a period of several months.

After some period of aging, the DODCI treated sample is found to display a photoluminescence corrected for phototube and system response which exceeds the intensity of a nominally prepared PS substrate sample by a factor of five. Further, the distribution of fluorescence is notably broader with a peak response considerably red shifted (about 30–50 nm) from an aqueous etched untreated PS substrate sample. This is consistent with a PS-dye coupling. Note that, as opposed to high temperature annealing at temperatures between 100° C. and a very significant 600° C. for short periods to promote oxidation on the PS substrate surface, this embodiment shows a long-term aging process under conditions which promote the conversion of the surface and ensure a dye initiated modification without seriously modifying the interacting constituencies.

Simple immersion or prolonged soaking of the PS substrates in millimolar (mM) dye solutions is sufficient not only to position the dye in close proximity to the surface bound PS emission centers but also to promote its interaction. The most pronounced interaction is manifest for those samples treated in DODCI. The effects observed for both DODCI and Rhodamine 700 are greatest for those samples treated after aqueous etching.

A histogram with delays ranging from 0.5 to 61.5 μs (5 μs gate) for the DODCI treatment of an aqueous etched sample shows a convergence to a dominant feature peaking at about 650 nm. By comparison, a histogram of the PL for time delays of 0.5 to 11.5 μs (5 μs gate) demonstrates the evolution observed for an untreated aqueous etched sample. The DODCI treated sample is distinct, displaying initially both a "green" emission feature and an "orange-red-red" emission feature which at first appear to "bookend" the observed aqueous etch emission features. With increased delay time, the green emission feature red shifts and the red emission feature appears to split into two features, one of which blue shifts with increased delay time and a second peak which appears almost stationary in time. This gives the appearance of a triple peaked spectrum for time delays ranging from 7.5 to 23.5 μs. After a 27.5 μs delay, the shifting short wavelength and orange-red features have virtually merged into each other to form a dominant peak at about 640 nm which eventually red shifts by about 10 nm. The observed spectra after 27.5 μs suggest that the continued red shifting of the initially green emission feature somewhat dominates the observed time dependence. The peak spectral intensity observed in a given histogram remains virtually constant out to 33.5 μs.

The interaction of Rhodamine 700 with an aqueous etched PS substrate sample appears to be much less pronounced than that for DODCI. The shifting green and orange-red emission features have merged in the 7.5 μs delay scan to a dominant spectral peak at 640 nm which red shifts to 650 nm by 21.5 μs. Further, the drop off in spectral intensity occurs considerably more rapidly.

In another histogram obtained for a DODCI treated hybrid etched sample, initially soaked for 45 minutes in a $10^{-3}$ M dye solution, the dye has a clear affect on the hybrid etched sample although not as pronounced as that on the aqueous etched sample. Further, the extended period of exposure to the dye is required as a hybrid sample simply dipped in DODCI is found to rapidly converge to a strongly dominant 630–640 nm feature indicative of the untreated hybrid etch. In another histogram, the PL for the DODCI treated sample is compared to the evolution for an untreated hybrid etch sample for time delays of 0.5 to 9.5 μs (5 μs gate). The histograms display the cycle of convergence for the red shifting "green" and blue shifting "orange-red" emission features. However, the appearance of the triple peaked spectrum ($\tau_{delay}$~3.5 μs) and the time delay corresponding to the merging of the shorter wavelength and orange-red emission features to a dominant 630 nm (peak) feature, ~11.5 μs, occur on a considerably shorter time scale. The spectral intensity of the DODCI treated sample begins to drop off rapidly for time delays longer than 17.5 μs, converging to a final peak wavelength for the dominant feature at 650 nm.

A further histogram for a Rhodamine 700 treated hybrid etched sample suggests that even a 45 minute exposure has only a small effect. In fact, the convergence of the spectral features to a dominant single peak appears to occur even more rapidly than the untreated sample over the range of delay times 3.5 μs or less. A significant drop off in spectral intensity is observed to occur for time delays longer than 7.5 μs.

3. Metallization of PS Substrates

An existing challenge in fabricating PS devices rests with establishing electrical contact to the PS substrates. An exemplary embodiment of the present disclosure uses the methods of enhancement and stabilization of the PS substrates and the excited state fluorophors that can be created on the PS surface to enhance reduction (metallization) at the PS substrate surface. Embodiments of the present disclosure include using the excited state fluorophors, whose interaction and reducing capabilities are greatly enhanced relative to that of their ground states, to induce the deposition of the metal from a metal-containing solution onto the surface of the PS substrates. Metal ions can be reduced and deposited on the PS substrates and within the pores of the PS substrates. The deposition occurs in regions of the PS substrates that are illuminated with light from a light source (e.g. Xenon arc lamp, HeNe laser etc.). The illumination produces PL from the PS substrates which in turn causes metallization of the PS substrates. The thickness of the deposit upon the PS substrates is proportional to the time and intensity of exposure to the light source. While conventional electroless metal plating generally requires surface coating with Pd metal to catalyze the deposition process, exemplary embodiments of the present disclosure require no catalyst to deposit the metals of interest as the illuminated PS surface is itself catalyzing the deposition. These embodiments are therefore under non-catalytic conditions since no additional catalyst is needed to metallize the PS substrates.

More specifically, the post-etch method of electroless metallization of PS substrates includes treating the PS substrates with an $HCl(H_2O)$ solution. The PS substrates has a microporous framework on which is superimposed a nanoporous layer. The $HCl(H_2O)$ solution is at least 0.2M. In an exemplary embodiment, the $HCl(H_2O)$ solution includes an alcohol. The alcohols that may be used include, but are not limited to, ethanol, methanol, other appropriate alcohols for treating PS substrates, and any combination thereof. In another exemplary embodiment, the PS substrate is treated with an $HCl(H_2O)$ and alcohol solution. The next step, for both of the previous embodiments, includes treating the PS substrate with a hydrazine solution, which can remove fluorides from the porous silicon substrate. Thereafter, the PS substrate is introduced to a metal-containing solution. The metal-containing solution includes, but is not limited to, copper, silver, gold, and other appropriate electroless metals, and combinations thereof. Thereafter, the PS substrate is illuminated with a light source of less than about 750 nanometers. The light source includes, but is not limited to, a Xenon arc lamp, HeNe laser, or any other appropriate light source producing light of wavelength less than 750 nanometers for the metallization process. The illumination of the PS substrates causes the metal of the metal-containing solution to be reduced upon the surface and in the micropores and nanopores of the PS substrates. The PS substrate can also include a pattern or mask such that only portions of the PS substrate surface is metallized. The metallized PS substrate fabricated is capable of having resistances in the range of 20–1000 ohms. In addition, the metallized PS substrate can have a resistance in the range of 20–500 ohms. A preferred embodiment includes a metallized PS substrate that has a resistance in the range of 20–60 ohms.

EXAMPLE 3

Preparation of Metallized PS Samples

The following is a non-limiting illustrative example of an embodiment of the present disclosure which is discussed in more detail in Gole, et al., J. Electro. Soc., 147, 3785 (2000), which is herein incorporated by reference. This example is not intended to limit the scope of any embodiment of the present disclosure, but rather is intended to provide specific experimental conditions and results. Therefore, one skilled in the art would understand that many experimental conditions can be modified, but it is intended that these modifications are within the scope of the embodiments of this disclosure.

a. Preparation of PS Sample

As discussed for example 1, single crystal <100> boron doped silicon wafers with resistivities of about 50–100 ohm-cm were used in the current study. Both highly branched nanoporous and hybrid nanoporous covered microporous PS substrate samples were fabricated in an electrochemical cell constructed from high-density polyethylene. The working electrode was attached to the back of a p-type silicon wafer <100> (aluminum coated) and the counter electrode corresponded to a platinum foil placed in solution. The cell was sealed to the front of the wafer, using a clamp, as about a 1 cm$^2$ section of the wafer made contact with the solution. A magnetic stir-bar was used to prevent the build-up of hydrogen at the surface of the silicon. The electrochemical etching current was supplied by an Potentiostat/Galvanostat. The nanoporous samples were etched in an aqueous 25% HF in methanol solution while the hybrid samples were etched in a solution of 1M $H_2O$, 1M HF, and 0.1M tetrabutylammonium percholate (TBAP), all in acetonitrile. The aqueous etched samples were etched at a current density ranging from about 2 to 30 mA/cm$^2$ and preferably about 8 mA/cm$^2$ for about 50 to 75 minutes while the hybrid samples were etched with a current density of about 6 mA/cm$^2$ for between 50 and 75 min. Using this latter procedure, pores approximately 1 to 2 μm wide by about 10 μm deep were formed, and well covered by a coating of nanoporous silicon.

Further, as discussed in example 1, single-crystal <100>, boron-doped silicon wafers (substrate) of resistivity ranging from about 1 to about 50 ohm cm were also etched in an aqueous HF solution. For several of the experiments (about 20% concentration of HF in methanol), a 300-nm thin film of aluminum was sputtered onto the backside of the wafers. Electrical connections were made to the wafers by connecting a wire to the thin film of aluminum using conductive paint. The wire and aluminum film were then covered with a layer of black wax, leaving only the front surface of the silicon exposed to the etching solution. Both the wired silicon-wafer as one electrode and a platinum wire as a counter-electrode could be connected through a Teflon cap, which was tightly fitted to a cuvette containing the etch solution. Ohmic contacts were made to the wafer by connecting a wire to the thin film of aluminum using conductive paint. Etching currents ranged from about 2 to 30 mA/cm$^2$, but the samples considered here were usually etched at 8 mA/cm$^2$ for 10 minutes.

After the nanoporous and hybrid etches were complete, the samples were removed to air, washed with methanol, and dried. For the majority of the samples, the etched PS substrate samples were treated with anhydrous concentrated hydrazine (about 30 M) to remove fluorine from the surface via a reaction which converts the fluorine and hydrazine to nitrogen and HF.

b. PL Stabilization Using HCl

Several of the samples were later treated with a 6M HCl/MeOH solution to: (1) enhance the photoluminescence and (2) stabilize the photoluminescence quantum yield.

c. Preparation of the Electroless Plating Solution

An electroless copper solution was prepared, following standard procedures known in the art, from $CuSO_4.5H_2O$ (0.76 g), sodium potassium tartrate (4.92 g), formaldehyde (2 ml), and NaOH (0.80 g) diluted to 200 ml in doubly de-ionized water. A slightly modified procedure was used to prepare an electroless silver solution. First 0.75 M $NH_4NO_3$ (12 g/200 ml) and 2 M $NH_3$ (24.3 mL $NH_4OH$/ZOO ml $H_2O$) solutions were mixed together and diluted in a 100 mL volumetric flask with doubly ionized water. To this solution was added 0.09 M $AgNO_3$ (1.36 g $AgNO_3$/200 ml) followed by 0.1 M $Co(NO_3)_2.6H_2O$ (5.82 g diluted into 50 ml of doubly de-ionized water). To this mixture was added sufficient doubly de-ionized water to bring the total solution volume to 200 ml. The copper and silver solutions were maintained in a refrigerator at 20° C. until they were used. As discussed above, other metal-containing solutions can be produced and used.

d. Metallization

Both the nanoporous and hybrid macroporous-nanoporous PS samples were exposed to the copper and silver electroless solutions either directly or after the samples were treated with HCl. The majority of the samples were also treated with anhydrous hydrazine. Samples were exposed directly to the electroless solutions both under ultraviolet/visible (UV/Vis) and HeNe laser photoluminescence excitation (PLE), in complete darkness, or in the presence of laboratory room lights. The observation of the reduction of the electroless solution metallic ions and the subsequent metal deposition was found to be surface illumination dependent.

The nature of the contact formation to the PS surface formed from <100> p-type silicon is now discussed. To place electroless metal contacts on the PS surface, this surface was first passivated with a non-stoichiometric silicon nitride, $SiN_x$, layer which was grown by plasma enhanced chemical vapor deposition, PECVD. The openings in the $SiN_x$ layer needed for formation of the porous layer were made by reactive ion etching, RIE. After an anodic etch, the porous layer was prepared and electroless copper (Cu) or silver (Ag) was deposited on the surface of this PS substrate layer to form the metal contacts necessary to make a resistance measurement.

Data was obtained for PS substrate samples exposed to electroless Ag and Cu solutions at about 16 and 30° C. For the vast majority of these experiments the samples were bathed in anhydrous hydrazine for periods of 30, 60, or 90 minutes before exposure in the electroless solutions. This treatment was carried out to remove fluorine based constituents from the PS substrate surface. With the removal of fluorine, the effects of optical pumping as it produces a long-lived photoluminescent emitter, can be readily evaluated. PS substrate samples, which are photoluminescent, are capable of plating silver and copper from an electroless solution, in which they are in contact, if exposed to uv/visible light or when exposed to a HeNe laser. If the PS surface is not photoluminescent or the PL from a photoluminescent surface is quenched, the deposition of copper or silver is diminished or completely absent. While temperature is an important consideration in these experiments, measurements of the very small surface temperature change as a function of exposure to the light sources used in this study demonstrate that the metal plating is not the result of a surface heating effect. However, an increased ambient temperature for the PS substrate surface, especially for those experiments involving electroless silver plating, can lead to an enhancement of the deposition process. In other words, the plating is more pronounced and more difficult to control precisely at 30° C. than at 16° C.

Photoluminescent PS substrate samples were clamped to the surface of a hollow copper block whose temperature could be adjusted by flowing water through a slush bath configuration at room or ice temperatures. Simultaneously, the sample under study was placed under a ring used to hold the electroless solution as the entire experiment was carried out under a flowing stream of high purity argon. Over the course of an experiment, the surface temperature was measured with a thermocouple. While this system could be operated at temperatures considerably lower than the ice bath temperature, $T_{surface}$(measured)=16±1° C., it was found that: (1) this was unnecessary to control the electroless process; and (2) that colder device temperatures eventually led to the undesirable condensation of the electroless solution. The temperature rise associated or induced by the high intensity uv/visible lamp, never exceeded 1.5° C. No temperature rise was recorded for those experiments with the HeNe laser (even if the laser was focused onto the tip of the thermocouple).

The reduction of silver from the electroless solution was found to be considerably more efficient than was that of copper from its electroless solution. For the silver samples at 16° C., hydrazine exposure was systematically varied from 30 to 60 to 90 seconds demonstrating only a moderate effect with increased exposure on the observed plating. Samples treated with hydrazine plate at a much slower rate than do untreated samples which have maintained a fluoride constituency on the PS substrate surface. Results were obtained for both aqueous etched and hybrid etched samples, the latter interacting with the electroless solutions notably more effectively.

SEM micrographs of copper and silver deposition into the pores of a hybrid macroporous/nanoporous sample at 16° C. demonstrate the deposition of metal to the walls of the micropores. The results of the resistance measurements on the initially generated electroless copper connections indicate resistances ranging from about 20 ohms to about 1000 ohms.

The electroless copper solution used in these experiments is considerably more stable (kinetically) than the electroless silver solution. In contrast to a freshly formed PS substrate surface, there is no plating on a c-Si substrate from the electroless copper solution and likewise there is no plating on PS substrate samples which have been oxidized in air for periods exceeding several weeks. As a freshly formed photoluminescent sample readily plates copper at room temperature, the plating ability of a PS substrate sample which has been subjected to extended oxidation can be restored with a brief exposure to a HCl solution. Samples which are exposed to the electroless copper bath will generally not plate copper if they: (1) are placed in a darkened location; (2) are soaked in etching solution in the absence of current flow before exposure; (3) are a heated at their surface in the presence of the electroless bath; or (4) have undergone a previous PL quenching process.

Thus, the plating process appears to require, at least in part, that a treated PS substrate surface be photoluminescent. However, it is known in the art that copper can be reductively deposited, in small concentration, on a PS substrate surface from an aqueous $Cu^{+2}$ solution in the absence of photoexcitation. Thus, anhydrous hydrazine has been introduced to modify the initially prepared PS substrate as a means of removing the fluoride centers on the surface, which may act as reducing centers for $Cu^{+2}$ (aq) ions. Upon treatment with hydrazine the copper reduction at the PS substrate surface (1) is slowed to an extent which allows a significant improvement in the degree of control of the metallization process, (2) clearly becomes a function of surface excited state fluorophors, and (3) is notably more amenable to pattern formation. The exposure of an untreated PS substrate surface, with its surface fluoride constituency, to the HeNe laser produces a photodefineable pattern in 5 minutes whereas the pattern produced with a Xe ArC lamp, with a plating time approaching one minute, is not photodefineable. Surface fluoride, like palladium, appears to act as a catalyst for the reduction process.

The PS substrates, whose luminescence has been quenched, cannot be patterned by the present method. While the mechanism of electroless deposition onto PS might result in part from electron-hole pair generation within the PS substrates it more likely results from excited state electron transfer involving surface-confined silicon oxyhydrides.

4. PS Sensors

The following is a non-limiting illustrative example of an embodiment of the present disclosure. For more information relating to embodiments of the present disclosure, see Seals, et al., J. Applied Physics, 91, 2519 (2000) and Gole, et al., J. Electrochem. Soc., 147, 3785 (2000), which are herein incorporated by reference. This example is not intended to limit the scope of any embodiment of the present disclosure, but rather is intended to provide specific experimental conditions and results. Therefore, one skilled in the art would understand that many experimental conditions can be modified, but it is intended that these modifications are within the scope of the embodiments of this disclosure.

Embodiments of the present disclosure provide for a PS sensor. The PS sensor includes a silicon substrate, a PS layer on a portion of the silicon substrate, and a front contact disposed onto a portion of the PS region. The PS region can include a nanoporous or a macroporous and nanoporous hybrid framework. In the preferred embodiment, the front contact can be disposed within the macroporous and nanoporous hybrid framework as well as extend above the PS region. The front contact can include one or more front contact portions made of metals such as, for example, copper, silver, and gold.

The PS sensors can be used to detect gases or liquids. The PS sensors have a contact resistance between the front contact and the PS between about 10 and 100 ohms, 20 to 100 ohms, and preferably about 20 and 60 ohms. In addition, the PS sensors have a resistivity between about 0.01 ohm cm to 10 ohm cm, and preferably about 0.1 ohm cm to 1 ohm cm, where the resistivity includes the PS region. The PS sensors operate at a bias voltage of between about 1 and 20 millivolts, and preferably about 1 to 10 millivolts. In addition, the PS sensors have a sensitivity of between about 10 and 100 parts per million (ppm). However, the sensitivity may be lower since it is difficult to acquire an independently verified sample below 10 ppm. The contact resistance, the resistivity, the operating bias voltage, and the sensitivity of the PS sensors should be contrasted to other gas sensors that have a preading resistance of about 200 kiloohms to 1 megaohm, have operating voltages between about 2 to 5 volts, and have a sensitivity between about 100 and 1000 ppm.

The PS sensor can be used in a variety of ways including, but not limited to, a stand-alone detector, an array of stand-alone detectors, a detector for gas chromatography (e.g., miniature gas chromatography), a detector for liquid chromatography, or a biosensor. Gas chromatographs, liquid chromatographs, and biosensors are well known in the art. The PS sensor can be used to detect gases (e.g., combustion generated gases such as carbon monoxide, carbon dioxide, sulfur dioxides, nitrogen oxides, hydrogen sulfide, and hydrogen cyanide) and liquids (e.g., organic, inorganic, and biological based liquid). In particular, PS gas sensors, in accordance with the present disclosure, can have a rapid and reversible response to analyte gases (e.g., hydrochloric acid, ammonia, and nitric oxide) at room temperature.

In some embodiments, the PS sensor can be used in conjunction with a selective film (e.g., metal, metal oxide, metalloid, metalloid oxide, non-metal, or biomolecular film) or a thin film of a catalytic material incorporated into the PS macroporous/nanoporous structure. For example, the PS layer of the PS sensor can be coated with a thin layer of metal such that the metal penetrates within the PS macroporous/nanoporous structure. The metals can include, but are not limited to, palladium (Pd), iridium (Ir), rhodium (Rh), vanadium (Va), and ruthenium (Ru). In this regard, the PS sensor can be designed to provide selectivity for a particular gas/liquid.

In another example, a nanostructure (e.g., a nanosphere, a nanowire, a nanodisk, and a nanobelt) and/or a coated nanostructure (i.e., a nanostructure having a material (e.g., a metal, a metal oxide, metalloid, or metalloid oxide) disposed on the nanostructure) can be incorporated into the macroporous/nanoporous framework of the PS layer. For example, the nanostructure can be made of materials such as, but not limited to, oxide, silicon (Si), tin (Sn), chromium (Cr), iron (Fe), nickel (Ni), silver (Ag), titanium (Ti), cobalt (Co), zinc (Zn), platinum (Pt), palladium (Pd), osmium (Qs), gold (Au), lead (Pb), iridium (Ir), molybdenum (Mo), vanadium (V), aluminum (Al), silicon oxide ($SiO_x$), tin dioxide ($SnO_2$), chromia ($Cr_2O_3$), iron oxide ($Fe_2O_3$, $Fe_3O_4$, or FeO), nickel oxide (NiO), silver oxide (AgO), titanium oxide ($TiO_2$), cobalt oxide ($Co_2O_3$, $Co_3O_4$, or CoO), zinc oxide (ZnO), platinum oxide (PtO), palladium oxide (PdO), vanadium oxide ($VO_2$), molybdenum oxide ($MoO_2$), lead oxide (PbO), titanium oxide ($TiO_x$), titanium nitride ($TiN_x$), titanium oxinitride ($TiO_xN_y$), and combinations thereof. In this regard, the PS sensor can be designed to provide selectivity for a particular gas/liquid.

In still another embodiment, a portion of the PS region 19 can be coated with a thin film of a biomolecule to enhance the selectivity of the PS sensor towards a particular gas or liquid (e.g., glucose). For example, the PS region 19 can be coated with a thin layer of a biomolecule such as, for example, an antibody, a polypeptide, or a polynucleotide.

In addition, an array of PS sensors can be used to enhance sensing selectivity as the array of PS sensors provide multiple data points per tested sample and can be modified to provide selectivity for one gas/liquid over another in various regions of the PS sensor array. Thus, the array of PS sensors can include PS sensors sensitive to select gases and/or liquids. In this regard, the array of PS sensors can detect multiple analytes simultaneously, while also enhancing sensing selectivity.

Figure 1B:
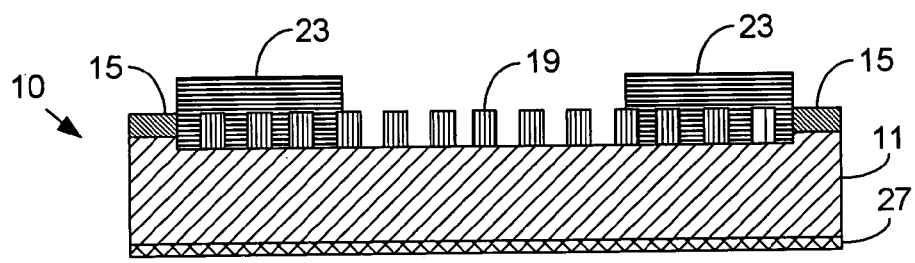
FIG. 1B is a cross-sectional view of the porous silicon sensor shown in FIG. 1A in the A—A direction.

FIG. 1A illustrates a top view of a PS sensor 10, while FIG. 1B illustrates a cross-sectional view of the PS sensor 10 in the A—A direction shown in FIG. 1A. The PS sensor 10 shown in FIGS. 1A and 1B includes a silicon substrate 11, a $SiN_x$ layer 15, a PS layer 19, and a front contact 23. In addition, the PS sensor 10 can include a backside contact 27, however this is optional.

The $SiN_x$ layer 15 is disposed on the silicon substrate 11. The PS layer 19 is fabricated from the silicon substrate 11 using techniques discussed above to form a nanoporous (not depicted in FIGS. 1A and 1B) or a macroporous/nanoporous PS framework. As depicted in FIG. 1B, a portion of the front contact 23 is disposed in the PS layer 19, while the remaining portion of the front contact 23 extends above the PS layer 19. In other words, the front contact 23 is included within the macroporous/nanoporous regions of the PS layer 19, which achieves a lower contact resistance between the front contact 23 and the PS layer 19. Alternatively, the front contact 23 can be disposed on top of the PS layer 19.

The silicon substrate 11 can include wafers, such as, but not limited to, silicon wafers, doped silicon wafers, p-type silicon wafers, and boron doped silicon wafers. The silicon substrate 11 can have dimensions appropriate to form a PS region as well as appropriate for a particular application. The $SiN_x$ layer 15 can be deposited using PECVD (plasma enhanced chemical vapor deposition) at about 200° C. to 300° C., and preferably at 250° C. in a Plasma Therm™ (St. Petersburgh, Fla.). The $SiN_x$ layer can be between about 100 to 300 nanometers (nm) thick, and preferably 200 nm thick. Other materials can be used in place of the $SiN_x$ layer 15 such as, but not limited to, a polymer layer, a $SiO_xN_y$ layer, an insulating dielectric film, a ceramic layer, photoresist layer, and polyimide layer.

The PS region 19 can include a nanoporous region, or preferably a macroporous/nanoporous framework (i.e., a macroporous framework on which is superimposed a nanoporous layer). The macroporous framework can include pores approximately 1 to 2 μm wide and about 10 μm deep, while also having nanopores throughout the macroporous framework. The PS region 19 can be prepared by electrochemically etching a portion of the silicon substrate with acetonitrile, hydrogen fluoride, and TBAP, for example. The photoluminescence (PL) of the PS region can be enhanced and stabilized by treating the PS region 19 with a solution that can include components such as, but not limited to, an aqueous hydrochloric and aqueous hydrochloric acid/alcohol solution. Additional details regarding the preparation of the PS region 19, and enhancement and stabilization of the PL of the PS region 19 are presented in more detail above.

As described above, the front contact 23 can be disposed within the PS region 19. In general, the front contact is formed by exposing the PS region 19 to a metal-containing solution and illuminating portions of the PS region 19 with an appropriate light source, as discussed above. The illumination causes PL of selected portions of the PS region 19, which causes the metal to metallize to the selected portions of the PS region 19. Additional details regarding metallization are described above.

The front contact 23 includes two contacts (as shown in FIGS. 1A and 1B). However, the front contact 23 can include one or more contacts (i.e., four contacts). In addition, the configuration of the front contact 23 can include additional configurations to the two shown in FIGS. 1A and 1B, and 2A and 2B. The front contact 23 can be made of metals, such as, but not limited to, gold (Au), silver (Ag), and copper (Cu). In addition, the front contact 23 can be made of conductive metal oxides such as, but not limited to, indium tin oxide ($InSnO_2$) and ruthenium oxide ($RuO_2$).

The backside contact 27 can be made of metal, such as, but not limited to, aluminum (Al), copper (Cu), tungsten (W), chromium (Cr), gallium (Ga), and gold (Au). In addition, the front contact 23 can be made of conductive metal oxides such as, but not limited to, indium tin oxide ($InSnO_2$) and ruthenium oxide ($RuO_2$). The backside contact 27 is used to apply a direct current bias to the backside of the silicon substrate 11.

Figure 2A:
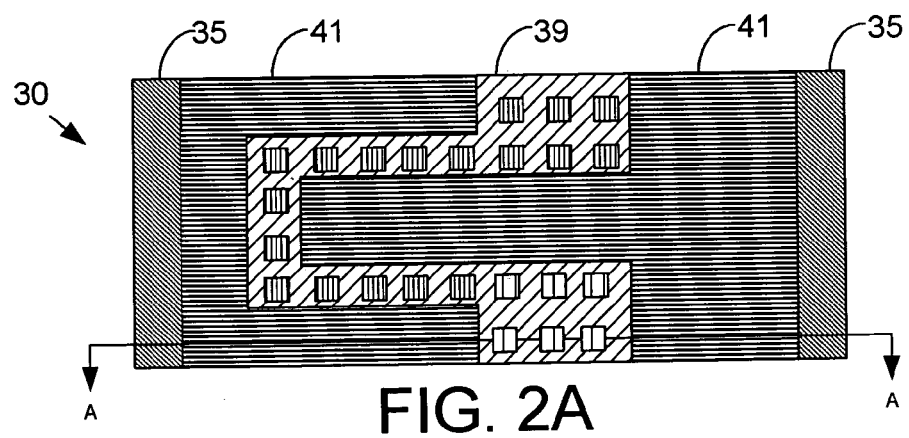
Figure 2B:
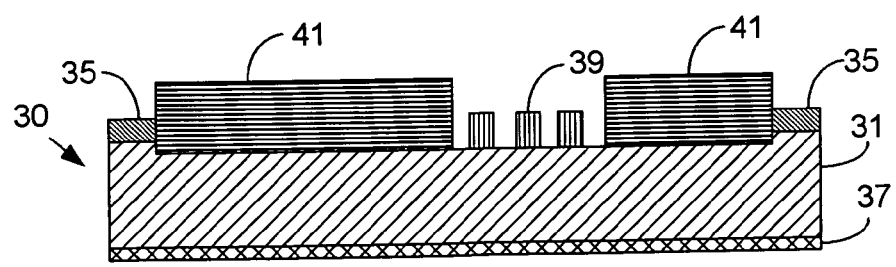
FIG. 2B is a cross-sectional view of the porous silicon sensor shown in FIG. 2A in the A—A direction.

FIG. 2A illustrates a top view of a PS gas sensor 30, while FIG. 2B illustrates a cross-sectional view of the PS gas sensor 30 in the A—A direction shown in FIG. 2A. The PS gas sensor 30 shown includes a silicon substrate 31, a $SiN_x$ layer 35, a PS layer 39, and a front contact 41. FIGS. 2A and 2B illustrate a different contact configuration. As indicated above, it is contemplated that additional contact configurations are possible and thus are included within the scope of this document. In addition, the PS gas sensor 30 can include a backside contact 37, however this is optional.

For the purposes of illustration only, and without limitation, embodiments of the present disclosure will be described with particular reference to the below-described fabrication method. Note that not every step in the process is described with reference to the process described in the figures hereinafter. Therefore, the following fabrication process is not intended to be an exhaustive list that includes every step required for the fabrication the embodiments of the PS sensor 10.

Figure 3A:
FIGS. 3A through 3K are cross-sectional views of a representative fabrication of the porous silicon sensor shown in FIGS. 1A and 1B.
Figure 3B:
Figure 3C:

FIGS. 3A–3K illustrate cross-section views of the PS sensor 10 shown in FIG. 1B during a representative fabrication process. FIG. 3A illustrates a silicon substrate 11 having an $SiN_x$ layer 15 disposed thereon. FIG. 3B illustrates a mask 17 disposed onto the $SiN_x$ layer 15, while FIG. 3C illustrates the patterning of the mask 17 into two mask regions 17A and 17B. The mask 17 can be made of materials such as, but not limited to, metals.

Figure 3D:
Figure 3E:

FIG. 3D illustrates the etching of the $SiN_x$ region 15 into two $SiN_x$ regions 15A and 15B using reactive ion etching. FIG. 3E illustrates the removal of the two mask regions 17A and 17B thereby exposing the two $SiN_x$ regions 15A and 15B.

Figure 3F:
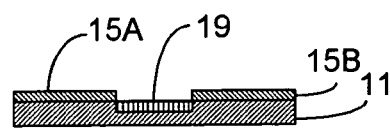

FIG. 3F illustrates the silicon substrate 11 after a portion of the silicon substrate 11 is electrochemically etched to form a PS region 19 disposed between the two $SiN_x$ regions 15A and 15B.

Figure 3G:
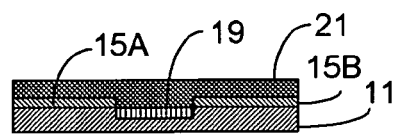
Figure 3H:
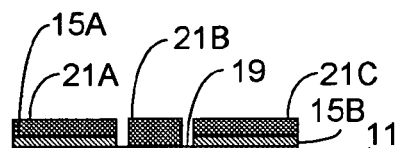

FIG. 3G illustrates a mask 21 disposed onto the two $SiN_x$ regions 15A and 15B and the PS region 19, while FIG. 3H illustrates the patterning of the mask 21 into three mask regions 21A, 21B, and 21C. The pattern of the mask regions 21A, 21B, and 21C exposes two portions of the PS region 19.

Figure 3I:
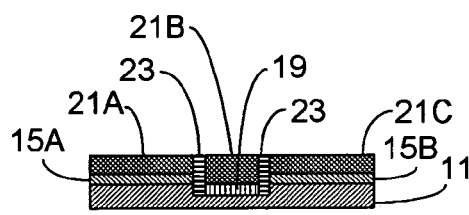

FIG. 3I illustrates the front contact 23 disposed onto the two portions of the PS region 19. The front contact 23 is disposed using the PL of the two PS regions 19 after the two PS regions 19 are illuminated with an appropriate light source, as discussed above. The front contact 23 can be disposed within the macroporous/nanoporous regions of the two PS regions 19. Alternatively, the front contact 23 can be disposed onto the two portions of the PS substrate 19 via techniques such as, but not limited to, electron-beam evaporation, sputtering, silk-screen printing, and electroplating.

Figure 3J:
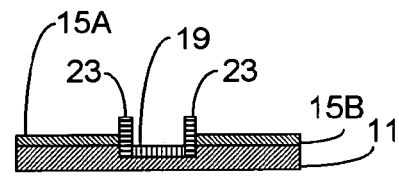
Figure 3K:
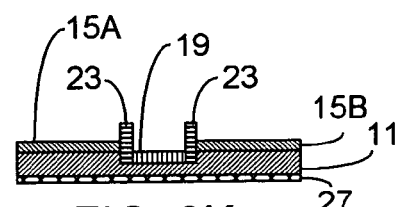

FIG. 3J illustrates the removal of the three mask regions 21A, 21B, and 21C, thereby exposing the front contact 23. FIG. 3K illustrates the backside contact 27 disposed onto the backside of the silicon substrate 11 using techniques such as, but not limited to, electron-beam evaporation, sputtering, silk-screen printing, and electroplating.

EXAMPLE 4 a. Preparation and Evaluation of a PS Sensor

The following is an illustrative example of an embodiment of a PS gas sensor in accordance with the present disclosure. Initially, cleaned (100) silicon wafers, [p-type, 2–20 ohm-cm, 2 inch diameter (available from Wafer World)] were covered with a 200 nm thick film of PECVD $SiN_x$ deposited at 250° C. in a Plasma Therm. The film thickness was measured with an elliposometer and the index of refraction was found to be about 1.8 at a wavelength of about 600 nanometers. A standard Shipley AZ 1827 positive photoresist process was used to pattern the $SiN_x$, which was subsequently removed by reactive ion etching in $CHF_3$ in the Plasma Therm™ (etch rate about 36 nanometers per minute). The exposed regions serve as the sites utilized for the PS region formation via electrochemical etching in a solution of 1M acetonitrile, 1M HF, and 0.1M TBAP, as described above.

The PS region formed has a hybrid structure that includes macropores impregnated by a nanoporous overcoat. Having formed a PS region, a second photolithography step is used for electrode definition. Electrical contacts produced by both electroless deposition (electro-less) and electron-beam evaporation (e-beam) have been found to produce a variety of resistances between about 28 ohms and 5 kilo-ohms. In the electroless process the walls for the hybrid structure of the PS region can be coated with a thin submicron film of the metals such as, for example, copper (Cu), silver (Ag), or gold (Au), which are reduced from the electroless solution, as described above. After contact formation, the resist is removed with acetone.

To facilitate bias measurements, an ohmic backside contact was applied to the backside of the silicon substrate. A 100 nanometer aluminum film was deposited by screen printing aluminum paste and rapid thermal annealing in an RP-10 (available from RPI systems, Inc.) for about 5 minutes at 850° C. Alloying leads to the formation a p+ layer of the silicon substrate in contact with the aluminum provides a low contact resistance between the aluminum metal and the silicon substrate. The high temperature alloying step does not appear to have any adverse effect on the PS layer. Thereafter, the modified silicon substrate was stored in dry nitrogen prior to packaging and wire bonding.

Thereafter, the PS gas sensor was mounted onto a 12 pin flat pack (available from OLIN AEGIS Inc.) and wire bonded with 1.5 mil gold wire to the contact pads. Silver epoxy (Ablebond 84-1LM that is available from Abelstick Company) was placed on the pad to strengthen the connection, which are at cured at room temperature.

b. Sensor Evaluation

The PS gas sensor was evaluated using an experimental setup that includes a small, ⅛th inch ID Tygon tubing sheathed onto ⅛th inch OD stainless steel tubing. The steel tubing was connected to a 150 millimeter Shield Industrial Flow meter (Air products, Inc.) and a stainless steel chamber, to which the PS gas sensor was mounted, with an internal volume approximately 1 $cm^3$. The PS gas sensor was electrically connected to a Solartron impedance analyzer (SI 1260, Solartron Mobrey, Houston, Tex.) and the impedance analyzer was connected to a PC computer for data acquisition running Z-view (Scribner Associates, Inc.). Open and short circuit calibrations were stored in the instrument to correct for cable impedance. The impedance of the PS gas sensor was measured over a frequency range 100 Hz to 20 KHz with an integration time of 1 second. The impedance was found to be frequency independent. The time response was measured at a fixed frequency of 1 kHz, generally with a 10 millivolt RMS drive voltage at room temperature.

A flow of nitrogen gas, controlled to a rate less than 1 sccm, was introduced to the reaction chamber. After the nitrogen flow was stopped, the test gas was introduced into the measurement cell. Gases tested included 100 ppm of HCl, $NH_3$, and NO in argon that were independently calibrated (Air Products). After approximately 30 seconds a pump was turned on to evacuate the measurement cell. Impedance readings were recorded to data files in a computer automatically.

Figure 4A:
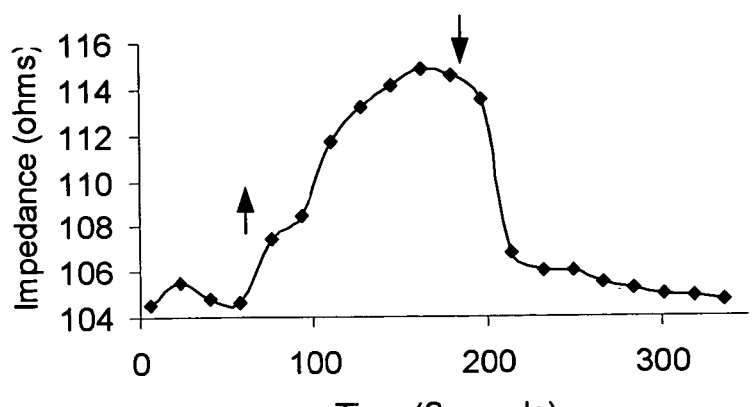
FIGS. 4A, 4B, and 4C are graphs plotting the response of a porous silicon sensor in response to exposure to hydrochloric acid, ammonia, and nitric oxide, respectively. The up arrow indicates the point at which the gas was introduced to the porous silicon sensor in a chamber, while the down arrow indicates the point at which the gas was evacuated from the chamber.
Figure 4B:
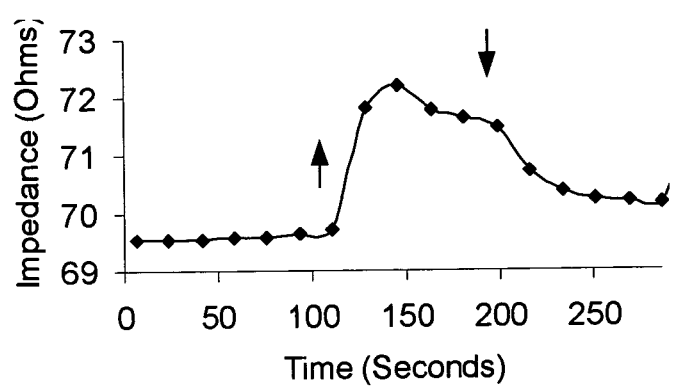
Figure 4C:
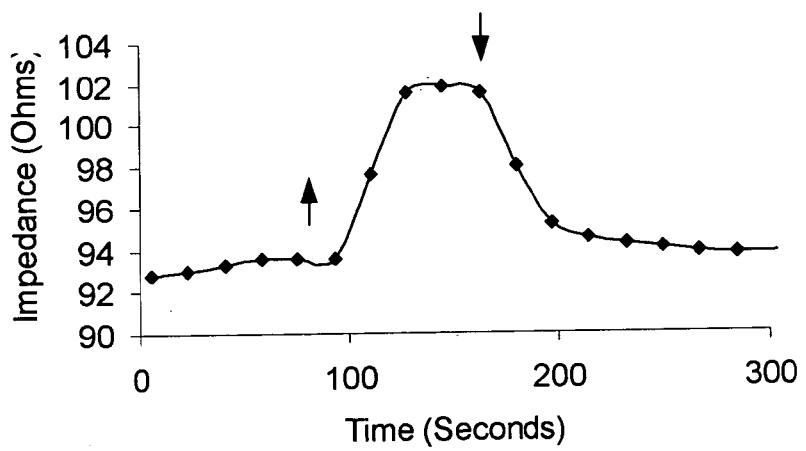

FIG. 4A through 4C depict the response of the interdigitated PS gas sensor to concentrations of 100 ppm of HCl, $NH_3$, and NO corresponding to a change of impedance of 8, 2.5, and 12 ohms respectively. The up arrow indicates the point at which the gas was introduced to the PS sensor in a reaction cell, while the down arrow indicates the point at which the gas was evacuated from the reaction cell. A rapid return of the impedance to its baseline impedance value occurred when the reaction cell was evacuated. Although, the absolute value of the impedance has changed somewhat due to some baseline drift, this is corrected for by determining the impedance prior to the experiment. Also note that the data presented in FIGS. 4A through 4C are taken for the highest resistance contacts employed in this study.

c. Discussion

The PS gas sensors in accordance with the present disclosure show a rapid and reversible response to the analyte gases at room temperature. Compared to the limited reports of conductometric PS gas sensors, the response is more sensitive, allowing the detection of HCl and ammonia and at a reduced applied DC bias. A rapid response suggests a surface reaction that is easily reversed. The response times indicate a time constant for all analytes on the order of 1 minute, however, this was strongly affected by the flow characteristics of the measurement system. In particular, the flow cell internal volume (1 $cm^3$) and flow rate of 1 sccm. Hence, the response time of the PS gas sensor itself may indeed be more rapid.

Absorption of molecules onto the porous silicon layer can be due to van-der Waals interactions, dipole-dipole interactions and/or electron exchange with surface states. The extent to which each is responsible in this case has yet to be determined. The magnitude of the response is a function of the analyte concentration (data not shown) indicating, for example, a larger impedance change at higher ammonia concentrations up to 1% ammonia in argon. For HCl, $NH_3$, and NO the magnitude of the response is not in agreement with the relative dipole moments of these gas molecules. This data suggests that a form of electron exchange, similar to that for the conductive metal oxides contributes to the channel conductivity modulation The PS gas sensor of the present disclosure is to be distinguished from those based on optical means of interrogation that have been or are currently being developed to make use of the PS photoluminescence employing (1) PL quenching, (2) laser interferometry, or (3) microcavity designs. The latter two approaches also represent more complex designs subject to more stringent fabrication and/or application procedures than the PS sensor discussed here.

Work on the electrical properties of PS has indicated that the film has a reduced number of carriers available for conduction. Also, some experiments suggest that Au/PS junctions might exhibit barrier heights of the order of 0.74 eV. While a barrier height can be sensitive to absorbed species, it appears that the low resistance of the PS gas sensors indicates a film based mechanism rather than barrier height modulation. The ohmic behavior of the contacts also supports this model; however, temperature dependent measurements of the junction electrical characteristics could be used to provide additional evidence.

The sensitivity of the PS sensor defined as the normalized resistance change per ppm of analyte concentration can be compared to other metal oxide sensors. For $NH_3$ and NO the sensitivity was 0.1%/ppm and for HCl 0.03%/ppm. This sensitivity is not as high as microfabricated $SnO_2$ sensors, which are typically 1%/ppm for reducing gases. However, the detection limits for $NH_3$ and NO depend upon the nano-structural properties of the $SnO_2$ and the manner in which it is prepared. Similar detection limits are possible for amperometric sensors like NASICON 28 with levels in the 0.1 ppm range. However, the sensitivities and response times of the PS gas sensor in accordance with the present disclosure are quite reasonable for a sensor operating at room temperature that has not been optimized for these analytes. For the data collected thus far at 100° C., the response of the PS gas sensor is notably more rapid. Further, the sensors operation at considerably higher partial pressures of HCl, $NH_3$, and NO extending to 1000 and 10,000 ppm is not compromised.

5. Sensors

The following is a non-limiting illustrative example of an embodiment of the present disclosure. For more information relating to embodiments of the present disclosure, see Example 5 below. This example is not intended to limit the scope of any embodiment of the present disclosure, but rather is intended to provide specific experimental conditions and results. Therefore, one skilled in the art would understand that many experimental conditions can be modified, but it is intended that these modifications be within the scope of the embodiments of this disclosure.

Embodiments of the present disclosure provide for conductometric PS gas sensors, methods of fabricating the conductometric PS gas sensors, methods of analyzing the data measured using the conductometric PS gas sensor, methods of selecting a conductometric PS gas sensor, methods of measuring the concentration of a gas, and methods of analyzing data.

The conductometric PS gas sensor (hereinafter "PS gas sensor") is operative to measure an impedance change that corresponds to a gas concentration (e.g., a gas concentration can be determined based on the impedance change or the magnitude of the impedance change) in at least 2 seconds. More particularly, the PS gas sensor transduces the presence of a gas into an impedance, which is measured by another device in communication with the PS gas sensor. Therefore, the term "measure" used in reference to the PS gas sensor can include the PS gas sensor in combination with another circuit or device (e.g., impedance analyzer, sensor and shunt circuit, and the like) to measure the impedance. It should be noted that the time frame for measuring the gas concentration depends, in part, on the particular application and gas being measured, but the concentration of the gas can be measured in at least 2 seconds in some embodiments, while in other embodiments, the time frame for measurement is longer. It should be noted that impedance includes contributions from one or more of resistance, capacitance, and inductance, and measurement of impedance includes the measurement of one or more of resistance, capacitance, and inductance.

The PS gas sensor includes a silicon substrate, a protective layer on a portion of the silicon substrate, a PS layer (or region) on a portion of the silicon substrate that is exposed through the protective layer, and two or more distinct contacts disposed onto a portion of the PS region and the protective layer. In another embodiment, a coating layer (e.g., a metal layer) can be disposed on the PS region not covered by the contacts, which enables the PS gas sensor to respond more strongly to certain gases relative to others depending on the metal used.

The protective layer can include, but is not limited to, a silicon carbide layer, a silicon nitride layer, a polymer layer, a silicon oxynitride ($SiO_xN_y$) layer, an insulating dielectric film, a ceramic layer, a photoresist layer, a polyimide layer, and combinations thereof. In an effort to be clear, the protective layer may be referred to as the silicon carbide layer hereinafter, but the protective layer could be any one of the layers described above in other embodiments.

The PS layer can include a nanoporous, a macroporous or a combined macroporous/nanoporous hybrid framework. The macropore is from about 0.5 to 20 μm and 0.5 to 10 μm deep, and the nanopores are about 1 to 2 μm in diameter. The contact can be disposed on and within the macroporous and nanoporous hybrid framework as well as extend above the PS layer and onto the silicon carbide layer. In other words, the material fills in a portion of the PS layer and then forms a layer on top of the PS layer. The contacts are distinct and separated from one another by a space (e.g., a portion of the PS layer and a portion of the silicon carbide layer). The contact can include one or more contact portions. In other words, one portion disposed on the PS layer and one portion disposed on the silicon carbide layer, but the two portions are contiguous in that a single metal layer extends from the PS layer onto the top of the PS layer and onto the silicon carbide layer. The contacts can be made of a metal or a combination of metals such as, for example, gold, copper, silver, titanium, and combinations thereof.

As mentioned above, the exposed portion of the porous silicon layer not covered by the contacts can be coated with a coating layer. The coating layer can include, but is not limited to, a metal layer, metal oxide layer, metal oxynitride layer, and combinations thereof. The coating layer can include, but is not limited to, tin (Sn), gold (Au), palladium (Pd), iridium (Ir), rhodium (Rh), vanadium (Va), ruthenium (Ru), platinum (Pt), titanium, oxides of each metal, oxynitrides of each metal, gold clustered oxides, and combinations thereof.

Embodiments of the PS gas sensor having a metal-coated porous silicon layer (coating layer) provide enhanced sensitivity (e.g., CO) and selectivity to certain gases (e.g., $NH_3$ in the presence of $NO_x$ (e.g., since NO reacts very fast the result is a mixture of NO and $NO_2$, which is generally called $NO_x$ where x is from 1 to 2). In particular, concentrations of select gases can be measured in the presence with one or more additional gases, where selected gases are more strongly sensed.

As briefly mentioned above, the PS gas sensor responds and is operative to measure an impedance change (e.g., an impedance magnitude change) across a first contact and a second contact that corresponds to a concentration of a gas. The sensitivity of the PS gas sensor is defined as the relative increase in impedance over a time frame following exposure to a concentration of a gas of interest. It should also be noted that the sensitivity is, in part, a function of the gas of interest, the gas mixture exposed to the PS gas sensor, the porous silicon layer, post processing of the porous silicon layer (e.g., cleaning with HCl), modifications to the porous silicon layer (e.g., disposing a coating layer on the porous silicon layer), the temperature of the system, the pressure of the system, and combinations thereof.

In general, the PS gas sensors have a gas detection lower limit of about 1 part per billion (ppb), which can be measured in as little as 2 seconds. In particular, the PS gas sensor is able to operate at, but is not limited to, ranges of gas concentrations including HCl from about 1 ppm to 0.1%, ammonia from 400 ppb to 0.1%, nitric oxide ($NO_x$) from 1 ppm to 0.1%, $SO_2$ from 1 ppm to 0.1%, $H_2S$ from 1 ppm to 0.1%, and CO from 5 ppm to 0.1%.

The operating parameters of the PS gas sensor include, but are not limited to, a bias voltage, an AC voltage frequency, an AC voltage amplitude and combinations thereof. The PS sensors operate at a bias voltage of between about 1 and 3000 millivolts, an AC voltage frequency between 100 and 100,000 Hz, an AC voltage amplitude of 1 and 1000 millivolts, or a combination thereof. The PS sensors operate preferably with no bias voltage, an AC voltage amplitude from 1 to 100 millivolts at an AC voltage frequency of 1000 Hz.

As mentioned briefly above, the impedance change can be measured with an impedance analyzer, a sensor and shunt circuit, or other impedance measurement devices. An embodiment of the sensor and shunt circuit uses a high impedance resistor in parallel with the sensor (PS sensor or components thereof). The resistor shunts the stray capacitance (removes high frequency noise), resulting in a resistive measurement.

The PS gas sensor can be used in a variety of ways including, but not limited to, a stand-alone detector, an array of stand-alone detectors, and a detector for gas chromatography (e.g., miniature gas chromatography). The PS gas sensor can be used to detect gases (e.g., combustion generated gases such as carbon monoxide, carbon dioxide, sulfur dioxides, nitrogen oxides, hydrogen sulfide, and hydrogen cyanide). In particular, PS gas sensors, in accordance with the present disclosure, can have a rapid and reversible response to analyte gases (e.g., including hydrogen chloride (HCl), ammonia ($NH_3$), carbon monoxide (CO), sulfur dioxide ($SO_2$), hydrogen sulfide ($H_2S$) and nitric oxide ($NO_x$)) at room temperature.

In addition, the PS gas sensor can be used as an array, where multiple PS gas sensors are uniquely sensitive to different gases of interest thereby enabling an array to measure the concentration of multiple gases simultaneously (e.g., the PS gas sensor is responds more strongly to one gas over a second gas). In addition, an array of PS gas sensors can be used to enhance sensing selectivity as the array of PS gas sensors provide multiple data points per tested sample and can be modified to provide selectivity for one gas over another on individual PS gas sensors within the PS gas sensor array. Thus, the array of PS gas sensors can include PS sensors sensitive to select gases. In this regard, the array of PS gas sensors can detect multiple analytes simultaneously, while also enhancing sensing selectivity.

In another example, a nanostructure (e.g., a nanosphere, a nanowire, a nanodisk, and a nanobelt) and/or a coated nanostructure (i.e., a nanostructure having a material (e.g., a metal, a metal oxide, metalloid, or metalloid oxide) disposed on the nanostructure) can be incorporated into the macroporous/nanoporous framework of the PS layer. For example, the nanostructure can be made of materials such as, but not limited to, metal oxides, silicon (Si), tin (Sn), chromium (Cr), iron (Fe), nickel (Ni), silver (Ag), titanium (Ti), cobalt (Co), zinc (Zn), platinum (Pt), palladium (Pd), osmium (Os), gold (Au), lead (Pb), iridium (Ir), molybdenum (Mo), vanadium (V), aluminum (Al), silicon oxide ($SiO_x$), tin oxide ($SnO_x$), chromia ($Cr_2O_3$), iron oxide ($Fe_2O_3$, $Fe_3O_4$, or FeO), nickel oxide (NiO), silver oxide (AgO), titanium oxide ($TiO_2$), cobalt oxide ($Co_2O_3$, $Co_3O_4$, or CoO), zinc oxide (ZnO), platinum oxide (PtO), palladium oxide (PdO), vanadium oxide ($VO_2$), molybdenum oxide ($MoO_2$), lead oxide (PbO), titanium oxide ($TiO_x$), titanium nitride ($TiN_x$), titanium oxinitride ($TiO_xN_y$), and combinations thereof. In this regard, by using these materials, the PS gas sensor can be designed to provide selectivity for a particular gas.

In general, the PS gas sensor can be fabricated by first providing a silicon substrate having a silicon carbide layer disposed on a first portion of the silicon substrate. Then, a first area on the silicon substrate is converted into a porous silicon layer, where the first area does not have a silicon carbide layer disposed thereon. Next, a first contact is formed onto a first portion of the porous silicon layer and onto a first portion of the silicon carbide layer. The first portion of the silicon carbide layer is contiguous with the first portion of the porous silicon layer as described above. A second contact is formed onto a second portion of the porous silicon layer and onto a second portion of the silicon carbide layer. The second portion of the silicon carbide layer is contiguous with the second portion of the porous silicon layer as described above. A third portion of the porous silicon layer is between the first portion and the second portion of the porous silicon layer. The first and second contacts are typically formed at the same time. In addition, the first and second contacts are typically formed using a shadow mask technique as described in more detail in Example 5.

Additional fabrication steps can be conducted. For example, an additional fabrication step includes cleaning the porous silicon layer with a mixture of one part hydrochloric acid (about 44%) in about five parts methanol for about four hours, for example. In addition, a fabrication step for forming a coating layer on the porous silicon layer can be performed. Additional details regarding the fabrication of the PS gas sensor are described in reference to FIGS. 6A through 6H and in Example 5.

After the PS gas sensor is formed, the PS gas sensor can be validated. In this regard, embodiments of this disclosure include methods of selecting a PS gas sensor having certain performance characteristics, methods of analyzing the data measured using the PS gas sensor, and methods of measuring the concentration of a gas. In addition, the method of validating includes detecting false positives (e.g., determining that an impedance change is not a response to a gas, but caused by another source). Furthermore, the present disclosure provides methods of analyzing data for the PS gas sensor as well as for other devices and sensors.

In general, the methods above include introducing a gas stream (e.g., including one or more gases of interest) to a PS gas sensor. Then, an impedance change is measured in the PS gas sensor. The impedance change can be measured with an impedance analyzer, a sensor shunt circuit (e.g, a resistor in parallel with the sensor to produce a resistance measurement), or other impedance measurement system. The impedance change can be used to validate (e.g., indicate that it has certain gas measurement characteristics and/or remove false positive responses) a gas sensor. In addition, impedance change (e.g., change in the magnitude of the impedance or a resistance) can be correlated to a gas concentration.

In particular, the methods mentioned above include introducing a gas to the PS gas sensor. The gas is exposed to the PS layer of the PS gas sensor, or in another embodiment where a coating layer (e.g., a metal layer or subsequently formed metal oxide layer) is disposed on the PS layer, the gas is exposed to the coating layer. Then an impedance change is measured across the first contact layer and the second contact layer. The impedance change can be further analyzed or can be correlated to the gas concentration.

The gas can be delivered to the PS gas sensor in a number of manners, such as, but not limited to, gas pulsing over a certain time frame, delivering gas packets, and delivering a constant gas flow. In one embodiment, the gas pulsing method can be used to measure a gas concentration in a noisy background. The gas pulsing method in conjunction with an algorithm (e.g., a transformation such as a fast Fourier transformation) described below can be used to measure a signal in the PS gas sensor or other sensor.

In general, the gas pulsing method of analyzing data includes pulsing a gas into a measurement device (e.g., a PS gas sensor) in a periodic manner. A change is measured in the measurement device that corresponds to a characteristic of the gas (e.g., concentration). The change is collected in a change data set. The change data set is analyzed using an algorithm (e.g., fast Fourier transformation (FFT) which can be used to obtain an FFT spectrum) to change the measured impedance from the time domain to the frequency domain. Then a time delay of the periodic pulses is measured. From this data, the characteristic of the gas for each pulse can be ascertained.

For example, in one embodiment in which the characteristic is concentration, the gas concentration can be determined by computing a magnitude of the impedance change, computing the time over which the magnitude of the impedance change occurs, and computing a slope from the ratio of the magnitude of the impedance change and the time.

In one embodiment of the gas pulsing method, the gas of interest can be exposed to the PS gas sensor in a periodic manner (e.g., for known time frame and repeated a plurality of times). In this embodiment, the impedance change measurements for the plurality of exposures are combined to form the impedance change data set. The impedance change data set can then be analyzed using a fast Fourier transformation (FFT) to produce an FFT spectrum, however, other transforms can be used instead of the FFT in other embodiments. In other words, the data set is transformed from the time domain to the frequency domain. Subsequently, a narrow region surrounding the period over which the gas was pulsed to obtain the FFT spectrum can be compared to a minimum performance parameter(s) and the PS gas sensor can be validated as performing above that threshold. In addition, the FFT spectrum can be analyzed to determine the time delay of the periodic pulses of the gas. Once the time delay is determined, the impedance change can be measured and correlated with the gas concentration.

For the gas pulsing method described above, given discrete values for the sampling rate, total test time, gas pulsing frequency, and a duty cycle of pulsed gas, a systematic routine can be produced to extract the impedance change associated with a given gas for a given duration over the surface of a PS gas sensor. The process of data analysis for quantification of a gas response can be divided into three functional components: FFT analysis, determination of the time delay, and solution extraction (i.e., impedance change determination and correlation to gas concentration). In the FFT analysis, the signal is transformed from the time domain to the frequency domain. The data is optionally filtered by a filter (e.g., in a band-pass manner and 3rd order Butterworth filter) such that only the frequencies of interest are analyzed. This phase also functions as a quality control measure that only allows devices with a reasonable frequency response to be further analyzed. The second component, determination of the time delay, involves a numeric analysis of the gas response data. This component calculates the response for all possible time delays. The time delays resulting in the maximum and minimum response are then obtained. This maximum and minimum (for a functioning device) are directly related to the gas pulsing rate, duty cycle, and linearity of response of the device, which determine the exact "on" and "off" times for the gas signal. Finally in the solution extraction module, the average response, the distribution of the response, and the dynamic trends of the response are computed and plotted.

The FFT analysis performs three functions. The first function is the input of the necessary signal and its transformation to the frequency domain. The second function is a basic filtering of the data and a recalculation of the frequency transform, although this step is not necessary in each embodiment. The final component, plotting of the respective transforms, allows a visual verification of the response of the sensor.

After the gas signal is transformed to the frequency domain, two functions are performed. The first function is validation of a gas response. For the PS gas sensor in the one embodiment, background noise associated with nitrogen pulsing around a 16 mHz band is quite low and not distinct from the surrounding frequencies. Furthermore, devices with a sensitivity to a given gas with an initial response time of less than 30 seconds, for example, result in strong frequency responses at this same band.

With this condition, a plot of the FFT spectrum for a gas exposed PS gas sensor offers simple methods for evaluating the quality and performance of PS gas sensors. While the experiment itself does not quantify all performance attributes, it is an effective means of screening a PS gas sensor for a match with minimum performance parameters. In an illustrative non-limited example, by fixing the period of the gas pulsing at 60 seconds, devices with initial response times much greater than 30 seconds will be automatically excluded. Additional parameters including the duty cycle, concentration, and operating temperature can be used to constrain "acceptable" devices.

The second function performed in this module provides an improvement on the minimum detection capability of the PS gas sensor by providing a capacity to filter components of the noise. Filtering offers an opportunity to remove or reduce the effects of periodic noise sources which include, but are not limited to, ambient pressure fluctuations, ambient temperature variations, systematic pressure and temperature fluctuations, additional environmental conditions, and combinations thereof. An illustrative filter includes a $3^{rd}$ order Butterworth filter.

Determination of the time delay acts as a secondary verification of data integrity and provides the algorithm with the exact start and stop points for the gas response of a PS gas sensor. The dynamic response of the PS gas sensor is being followed. An illustrative example of how the time delay is determined is described below.

The total response of the PS gas sensor is recorded versus time (into a data file) during, for example, a test consisting of 30 gas pulses, where the gas is turned on once per minute 30 seconds past the minute for thirty minutes, and the gas is turned off once per minute on the minute (for a total test time of 30 minutes). The data file's measurement of time will not have the same measurement of time as the start and stop time of the gas pulses being delivered, as there is a systematic delay between when a data point is measured by the impedance analyzer and when it is reported to the datafile. For example, if the gas was turned on at 3:05:30 in the real world, the response to this gas may be seen at 3:05:35 as reported in the data file. This systematic error (5 second delay) occurs for every pulse and is what is named the delay.

An illustrative example of how the time delay is determined is described below. A time delay is first assumed to be some time (such as 1 second). If this were the delay (i.e., when the gas pulse hits the device), we would expect to see a local maximum at 31 seconds (when the gas pulse is turned off), and a local minimum at 61 seconds (when the gas pulse is turned on). The values for the predicted local maximums (31 seconds, 91 seconds, . . . ) are added together, and then the values for the predicted local minimums (1 second, 61 seconds, 121 seconds, . . . ) are subtracted from that, resulting in a single number for the assumed 1 second delay. This process is repeated for all possible delays (delays of 1, 2, 3, . . . , 60 seconds for this example). The resulting data of the summed response is plotted vs. the delay. If the plot is sinusoidal, the maximums correspond to the time delay in the system, the minimums correspond to the average "recovery" of the sensor between pulses. If the plot is not sinusoidal, then the PS gas sensor is not acceptable. It should be noted that shorter time frames can be used, and the previous description is not limited to the time frames described.

Now having described the PS gas sensor and methods of evaluating the PS gas sensor, the following non-limiting figures are provided to provide additional details regarding the PS gas sensor and methods of evaluating the PS gas sensor.

Figure 5A:
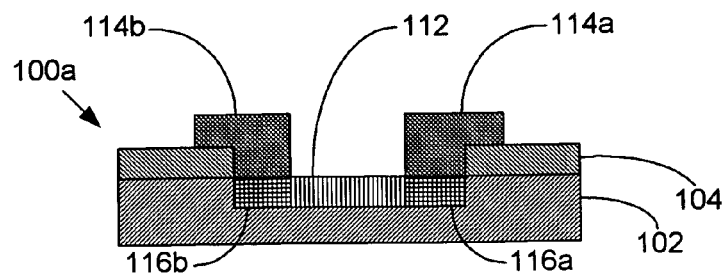
FIGS. 5A and 5B illustrate cross-section views of two embodiments of conductometric porous silicon (PS) gas sensors.
Figure 5B:
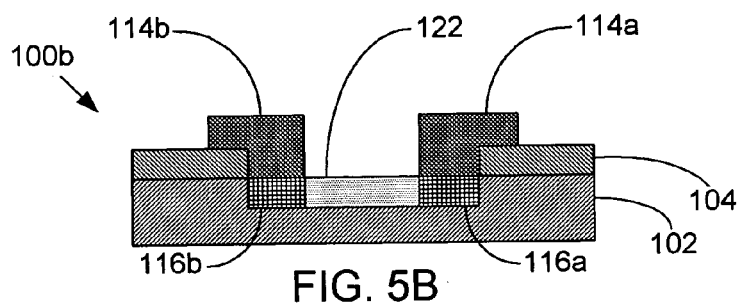

FIG. 5A illustrates a cross-sectional view of a PS gas sensor 100a, while FIG. 5B illustrates a cross-sectional view of a PS gas sensor 100b. The PS gas sensor 100a shown in FIG. 5A includes a silicon substrate 102, a silicon carbide layer 104, a PS layer 112, a first contact 114a, and a second contact 114b. The first contact 114a and the second contact 114b include a first PS metallized layer 116a and a second PS metallized layer 116b, respectively. As mentioned above in general, a first metal layer is disposed onto/within a first portion of the PS layer (first PS metallized layer 116a) and a first portion of the silicon carbide layer to form the first contact 114a, while a second metal layer is disposed onto/within a second portion of the PS layer (second PS metallized layer 116b) and a second portion of the silicon carbide layer to form the second contact 114b. The first portion of the silicon carbide layer is contiguous with the first portion of the porous silicon layer, while the second portion of the silicon carbide layer is contiguous with the second portion of the porous silicon layer. The first portion of the PS layer and the second portion of the PS layer are not contiguous and a space (e.g., PS layer between these two portions) separates the two layers. The first portion of the silicon carbide layer and the second portion of the silicon carbide layer are not contiguous and space (e.g., silicon carbide layer) separates the two layers. As a result, the first contact 114a and the second contact 114b are separated from one another. The PS gas sensor is operative to measure an impedance change across the first contact and the second contact that can correspond to a gas concentration present in the total gas exposed to the PS gas sensor.

The PS layer 112 is fabricated from the silicon substrate 102 using techniques discussed above to form a nanoporous or a macroporous/nanoporous PS framework. A portion of each of the first and second contacts 114a and 114b is disposed within the PS layer 112, while the remaining portion of the first and second contacts 114a and 114b are disposed above the framework and extend above the PS layer 112 onto the silicon carbide layer 104. In other words, the first and second contacts 114a and 114b are included within the macroporous/nanoporous regions of the PS layer 112, while the remaining portion of the contacts are disposed above the PS layer 112 and on a portion of the silicon carbide layer.

The silicon substrate 102 can include wafers, such as, but not limited to, silicon wafers, doped silicon wafers, p-type silicon wafers, and boron doped silicon wafers. The silicon substrate 102 can have dimensions appropriate to form a PS region as well as appropriate for a particular application. The silicon carbide layer 104 can be deposited using PECVD (plasma enhanced chemical vapor deposition) at about 200° C. to 300° C. and at about 500 to 1000 mTorr, and preferably at 250° C. and about 800 mTorr in a Unaxis PECVD. The silicon carbide layer 104 can be between about 100 to 500 nanometers (nm) thick, and preferably 200 nm thick. As mentioned above, other materials can be used in place of the silicon carbide layer 104 such as, but not limited to, a silicon nitride layer, a polymer layer, an SiO$_x$N$_y$ layer, an insulating dielectric film, a ceramic layer, a photoresist layer, and a polyimide layer.

The PS layer 112 is a macroporous/nanoporous framework (i.e., a macroporous framework on which is superimposed a nanoporous layer). The macroporous framework can include pores approximately 1 to 2 µm wide and from about 0.5 to 20 µm deep and about 0.5 to 10 µm deep, while also having nanopores throughout the macroporous framework located on the walls of the micropores. The PS layer 112 can be prepared by electrochemically etching a portion of the silicon substrate with acetonitrile, hydrofluoric acid, tetrabutylammonium-perchlorate (TBAP), and water, for example. Additional details regarding the preparation of the PS layer 112 are presented in more detail above.

As described above, the contacts 114a and 114b can be disposed within the PS layer 112 and on the silicon carbide layer 104. In general, the contacts 114a and 114b are formed by exposing the PS layer 112 using electron-beam metal evaporation or PL induced metallization, for example.

As shown in FIGS. 5A and 5B, the PS gas sensors 100a and 100b include two contacts 114a and 114b. However, additional contacts (i.e., four, five, or more contacts) can be used in other embodiments. The contacts 114a and 114b can be made of metals, such as, but not limited to, gold (Au), silver (Ag), copper (Cu), titanium (Ti), and combinations thereof.

For the purposes of illustration only, and without limitation, embodiments of the present disclosure will be described with particular reference to the below-described fabrication method. Note that not every step in the process is described with reference to the process described in the figures hereinafter. Therefore, the following fabrication process is not intended to be an exhaustive list that includes every step required for the fabrication of the embodiments of the PS gas sensors 100a.

Figure 6A:
FIGS. 6A–6H illustrate cross-section views of the conductometric PS gas sensors shown in FIG. 5A during a representative fabrication process.
Figure 6B:

FIGS. 6A–6H illustrate cross-section views of the PS gas sensors 100a shown in FIG. 5A during a representative fabrication process. FIG. 6A illustrates a silicon substrate 102 having a silicon carbide layer 104 disposed thereon. FIG. 6B illustrates a mask 106 disposed onto the silicon carbide layer 104. The mask 106 can be made of materials such as, but not limited to, metals.

Figure 6C:
Figure 6D:

FIG. 6C illustrates the etching of the silicon carbide layer 104 into two regions using reactive ion etching. FIG. 6D illustrates the removal of the mask 106 thereby exposing the two portions of the silicon carbide layer 104.

Figure 6E:
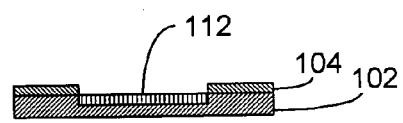

FIG. 6E illustrates the silicon substrate 102 after a portion of the silicon substrate 102 is electrochemically etched to form a PS region 112 disposed between the two portions of the silicon carbide layer 104.

Figure 6F:
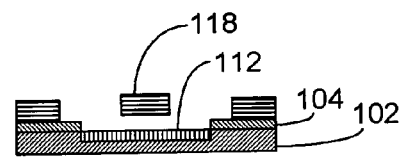

FIG. 6F illustrates a mask 118 (e.g., a shadow mask) disposed onto the silicon carbide layer 104 and the PS region 112. The pattern of the mask 118 exposes two portions of the PS region 112. The shadow mask can be made of a metal (e.g., copper), but the shadow mask can be made of other materials such as polymer, composites, and other masking materials. This step can be performed without exposing the PS region 112 to water, which is advantageous because the exposure of PS to water will result in the decreased sensitivity of the surface due to oxidation.

Figure 6G:
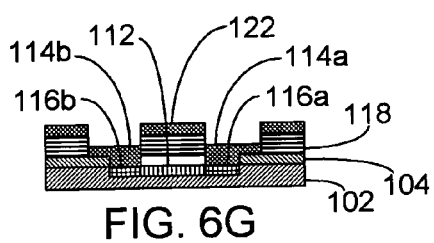

FIG. 6G illustrates the formation of the first contact 114a and the second contact 114b onto the two exposed portions of the PS region 112. The first contact 114a and the second contact 114b can be disposed within the macroporous/nanoporous regions (116a and 116b) of the PS region 112. A portion of the first contact 114a and the second contact 114b are also disposed on portions of the silicon carbide layer 104 (the spatial relationships are described in more detail above). The first contact 114a and the second contact 114b can be disposed onto the two portions of the PS substrate 112 via techniques such as, but not limited to, electron-beam evaporation, sputtering, silk-screen printing, electroless plating, and electroplating.

Figure 6H:
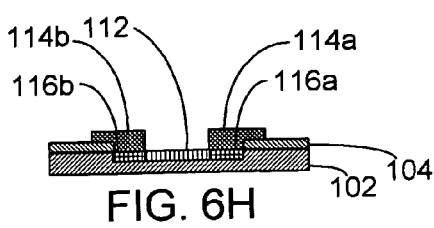

FIG. 6H illustrates the removal of the mask regions 118, thereby exposing the first contact 114a and the second contact 114b and the PS layer 112. Additional post processing steps can be performed on the structure. For example, the PS layer 112 can be treated with a mixture of HCl and methanol to enhance the gas detection characteristics. In addition, it should be noted that a coating layer (e.g., a metal layer) could be formed on the PS layer 112 in a subsequent step. The metal layer can be formed using techniques such as, but not limited to, electron-beam evaporation, sputtering, silk-screen printing, electroless plating, and electroplating.

Figure 7A:
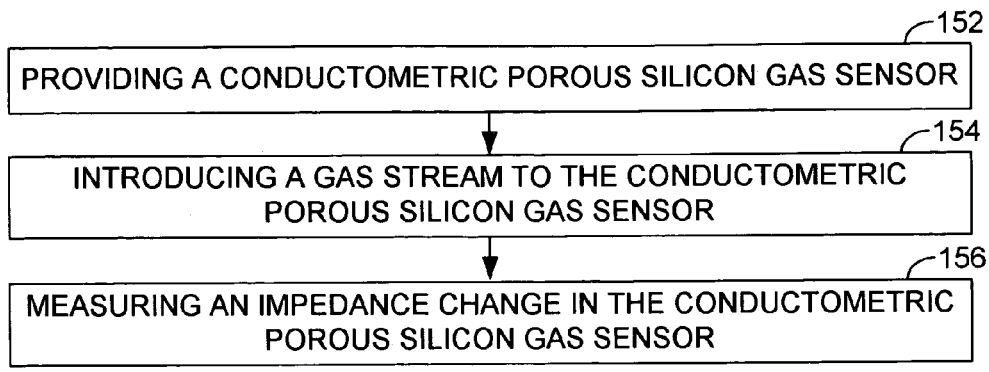
FIG. 7A is a flow chart describing an exemplary general flow of a method of evaluating a PS gas sensor.

FIG. 7A is a flow chart describing the general flow of a method of evaluating a PS gas sensor. In block 152, a PS gas sensor is provided. In block 154, a gas stream (e.g., one or more gases) is introduced to the PS gas sensor. In block 156, an impedance change is measured. As mentioned above and in more detail below, the impedance change can be further analyzed to validate the PS gas sensor and/or correlated to a gas concentration.

Figure 7B:
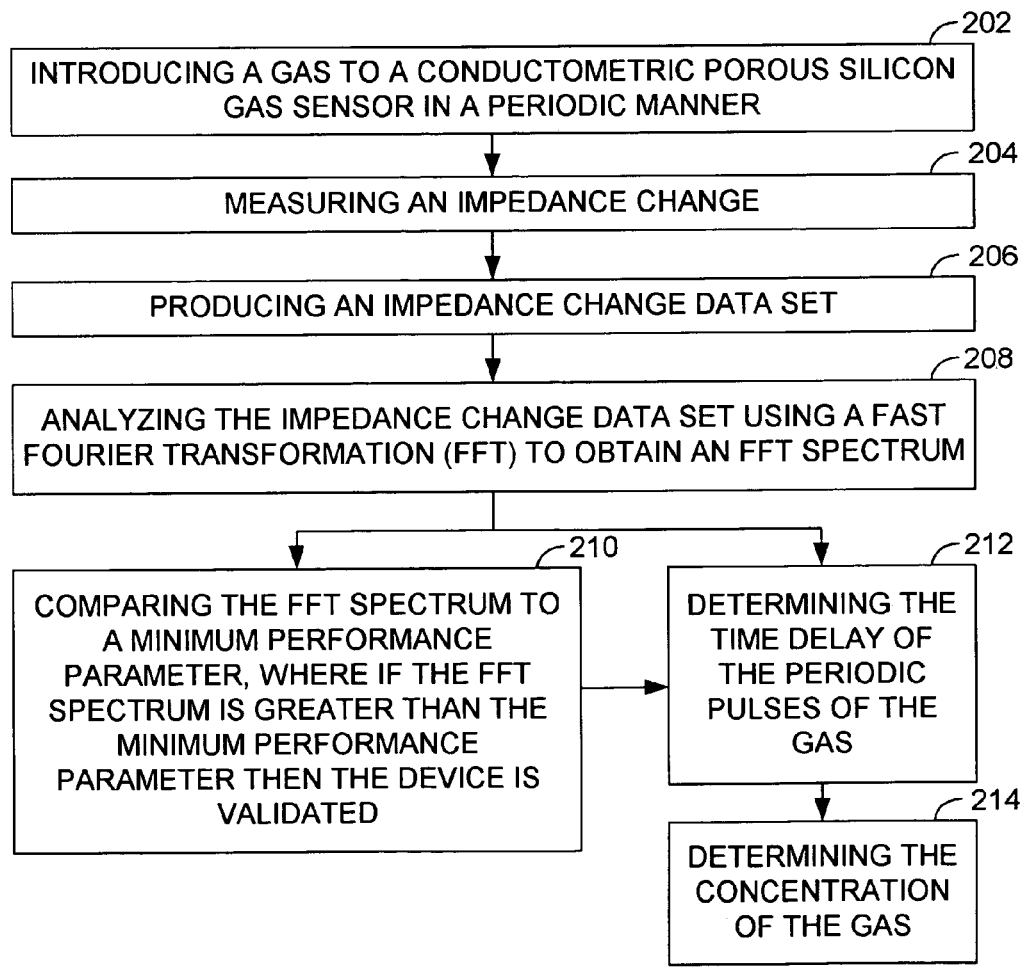
FIG. 7B is a representative flow chart of a process for evaluating a conductometric PS gas sensor.

FIG. 7B is a flow chart describing various embodiments of methods of selecting a PS gas sensor having certain performance characteristics, methods of analyzing the data measured using the PS gas sensor, and methods of measuring the concentration of a gas of interest. Various combinations of the flow chart are used to perform the methods described above. In block 202, a gas is introduced to a PS gas sensor in a periodic manner. In general, the gas is introduced to the PS gas sensor by pulsing a volume of gas into an area adjacent the PS gas sensor. In some embodiments, the gas pulsing can be controlled by turning a gas flow (on/off) from a gas source or mechanically blocking or re-routing the flow of the gas to the PS gas sensor. The source of the gas can be from an area in which the PS sensor is positioned, the gas can be pumped to a separate area in which the PS gas sensor is positioned, the gas can be encapsulated from a source and exposed to the PS gas sensor at a separate location, and the like. In any case, a carrier gas can be flowed while the gas is flowed and when the gas is not flowed past the PS gas sensor. The carrier gas can include, but is not limited to, air, nitrogen, nobel gases (e.g., argon), methane, carbon dioxide, and combinations thereof.

In block 204, an impedance change is measured. In general, the impedance change is measured across the first contact layer and the second contact layer. The gas interacts with the PS layer and causes an impedance change across the first contact layer and the second contact layer.

In block 206, an impedance change data set is produced. The impedance change data set corresponds to the periodic pulsing of the gas and the resulting impedance measurement. The impedance change data set can include a number of data points and can be adjusted to fit the particular purpose (e.g., validate the PS gas sensor, measure a gas concentration, etc).

In block 208, the impedance change data set is analyzed using a fast Fourier transformation (FFT) to obtain an FFT spectrum. Other transformations can be used in place of the FFT. The impedance change data set is transformed from the time domain to the frequency domain using an FFT analysis. Additional analyses can be performed, such as filtering the data set to remove noise sources (e.g., pressure fluctuations, random low frequency temperature effects, and the like). An example of a filter includes a Butterworth filter, however other filters can be used and one skilled in the art can select an appropriate filter.

At this point, the flow chart can proceed to block 210 or 212. The flow chart proceeds to block 210 for methods of selecting a PS gas sensor having certain performance characteristics, while the flow chart proceeds to block 212 for methods of analyzing the data measured using the PS gas sensor and methods of measuring the concentration of a gas of interest.

In block 210, the FFT spectrum is compared to a minimum performance parameter(s), where if the FFT spectrum is greater than the minimum performance parameter(s), the PS gas sensor is validated (e.g., is sensitive to a certain gas, gas concentration, response time, duty cycle, operating temperature, and the like for acceptable sensors). In an embodiment, the minimum performance parameter can be characterized as a comparison of impedance response when the gas is pulsed and when it is not pulsed. For example, the impedance response at the frequency that the gas was pulsed at is be much greater than the impedance at frequencies where no gas was pulsed. If they are about the same, no gas measurement has occurred. If they are significantly different, then a gas response has been detected. In this regard, false positives can be detected.

It should be noted that the flow chart could proceed from either block 208 or 210 to block 212. In block 212, the time delay is determined for the periodic pulses of the gas. The time delay module acts as a secondary verification of data integrity and provides the algorithm with the exact start and stop points for the gas response of a PS gas sensor. Additional details regarding the time delay are described herein.

In block 214, the concentration of the gas is determined. After the time delay is determined, the time at which the PS gas sensor was exposed to the gas is known. The data sets corresponding to each gas pulse can be extracted from the original as the response. Various numeric curve-fitting programs can be used to measure the impedance change, which corresponds to the concentration of the gas. Additional details regarding the concentration determination are described below.

Figure 8A:
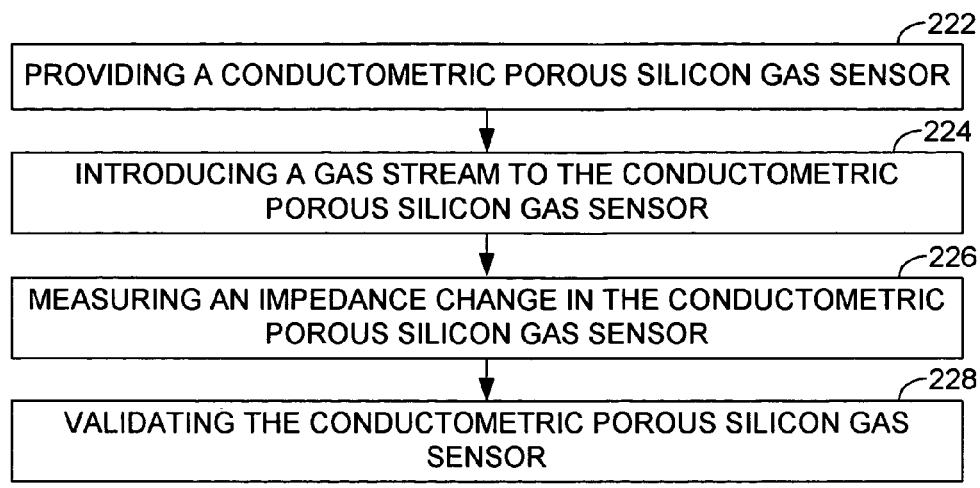
FIG. 8A is a flow chart describing an exemplary general flow for the validation of a PS gas sensor.

FIG. 8A is a flow chart describing a general flow for the validation of a PS gas sensor. In block 222, a PS gas sensor is provided. In block 224, a gas stream is introduced to the PS gas sensor. In block 226, an impedance change is measured in the PS gas sensor. In block 228, the PS gas sensor is validated (e.g., determining if the PS gas sensor is responding in an appropriate manner and/or determining if the response measured is a true response or a false positive).

Figure 8B:
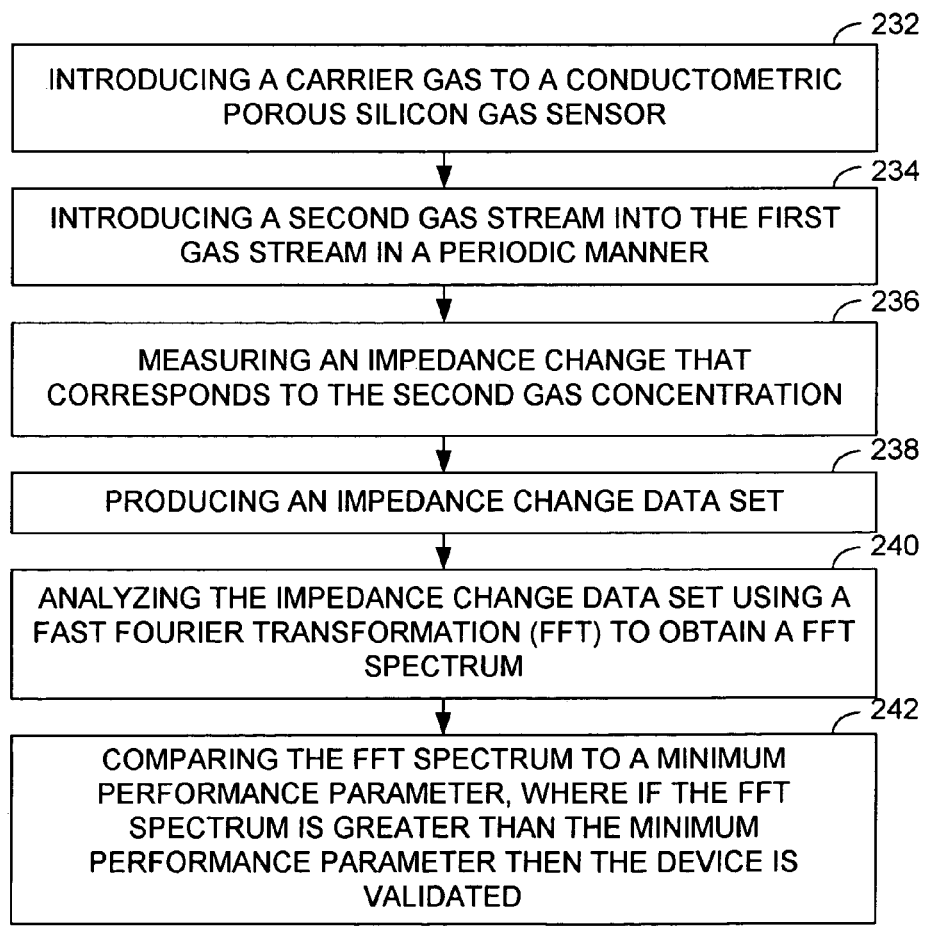
FIG. 8B is a representative flow chart of a process for evaluating a conductometric PS gas sensor.

In particular, FIG. 8B is a flow chart describing the validation of a PS gas sensor. In block 232, a carrier gas is introduced to the PS gas sensor. In particular, the carrier gas is exposed to the PS layer of the PS gas sensor.

In block 234, a second gas stream (e.g., a single gas or a gas mixture including the gas of interest) is introduced into the first gas stream in a periodic manner and exposed to the PS layer of the PS gas sensor. In this embodiment, the second gas stream is a single gas. In another embodiment, only a single gas stream (e.g., 1 or more gases can be present) is exposed (e.g., pulsed or continuous stream) to the PS gas sensor.

In block 236, an impedance change is measured, where the impedance change corresponds to the second gas concentration. The impedance change is measured as a function of time during the exposure of the second gas to the PS gas sensor. The time frame can be a few milliseconds to a few seconds to a few minutes, depending on the response time and the application of the PS gas sensor.

In block 238, an impedance change data set is produced. The impedance change data set corresponds to the periodic pulsing of the second gas and the resulting impedance measurement and can include a few points or many hundreds of points.

In block 240, the impedance change data set is analyzed using a fast Fourier transformation (FFT) to obtain an FFT spectrum. As mentioned above, the impedance change data set is transformed from the time domain to the frequency domain. An additional analysis that can be performed includes filtering the data set to remove noise sources as described above.

In block 242, the FFT spectrum is compared to a minimum performance parameter. If the FFT spectrum is greater than the minimum performance parameter then the PS gas sensor is validated. As mentioned above, the minimum performance parameter can be characterized as a comparison of the impedance response when the gas is pulsed and when it is not pulsed.

Figure 9A:
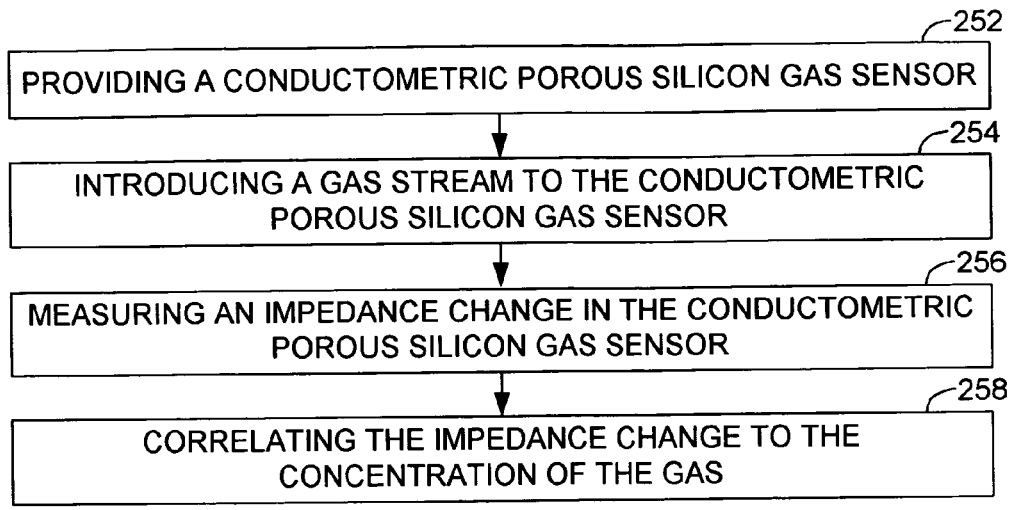
FIG. 9A is a representative flow chart of an exemplary general flow describing the correlation of the impedance change to the concentration of a gas.

FIG. 9A is a general flow chart describing the correlation of the impedance change to the concentration of a gas. In block 252, a PS gas sensor is provided. In block 254, a gas stream is introduced to the PS gas sensor. In block 256, an impedance change is measured in the PS gas sensor. In block 258, the impedance change is correlated to the concentration of the gas (e.g., the magnitude of the impedance change can be correlated to the concentration of the gas).

Figure 9B:
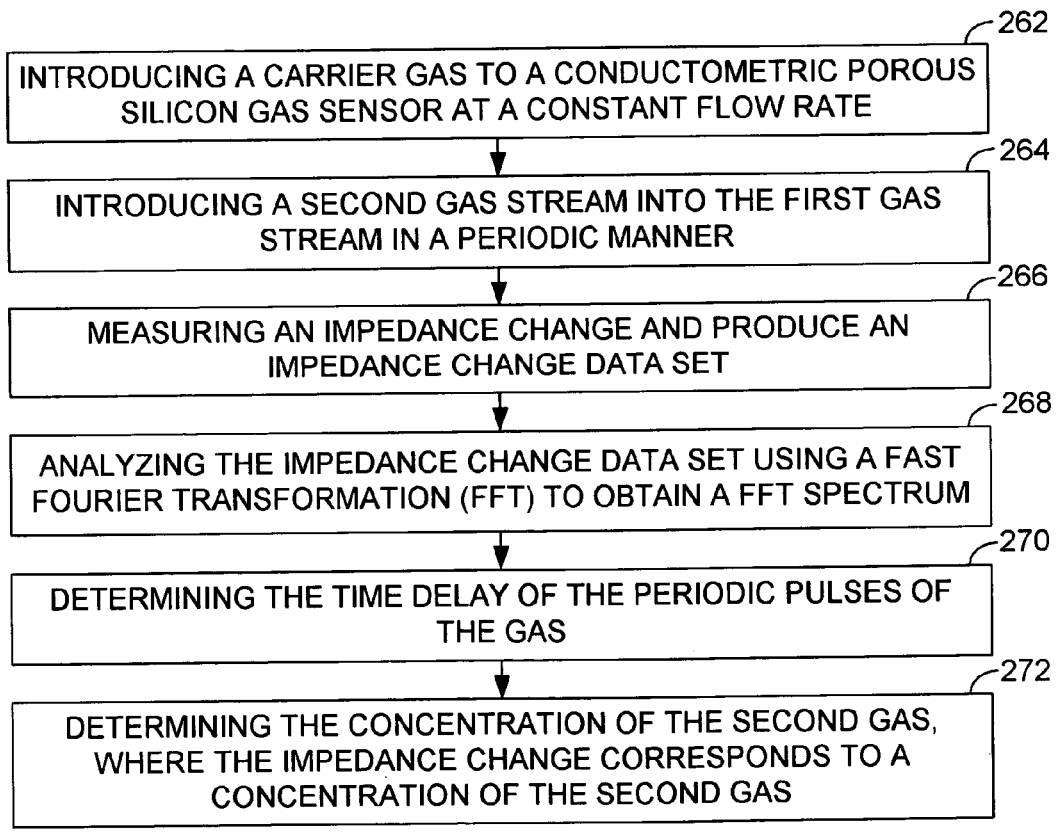
FIG. 9B is a representative flow chart of a process for determining the concentration of a gas using a conductometric PS gas sensor.

In particular, FIG. 9B is a flow chart for measuring a gas concentration using a PS gas sensor. In block 262, a carrier gas is introduced to the PS gas sensor at a constant flow rate as described above.

In block 264, a second gas stream (e.g., a single gas or a gas mixture including the gas of interest) is introduced into the first gas stream in a periodic manner and exposed to the PS layer of the PS gas sensor. In this embodiment, the second gas stream is typically a gas mixture. In an alternative embodiment, the second gas stream includes a single gas, where the original gas mixture has been separated into one or more different gases using, for example, gas chromatography.

In block 266, an impedance change is measured and an impedance change data set is produced, where the impedance change corresponds to the second gas concentration, as described in additional detail herein.

In block 268, the impedance change data set is analyzed using a fast Fourier transformation (FFT) to obtain an FFT spectrum, as described herein. In block 270, the time delay is determined for periodic pulses of the gas, as mentioned herein. In block 272, the concentration of the gas is determined in a manner as described above.

EXAMPLE 5

Conductometric porous silicon gas sensors (PS gas sensors) that include a sensitive surface layer that is conducive to the rapid and reversible transduction of sub-ppm levels of analyte gas are described. Several fabrication and testing methods allow the detection of a number of analytes including CO (<5 ppm), $NO_x$ (<1 ppm), $SO_2$ (<1 ppm), and $NH_3$ (500 ppb). A progression of fabrication techniques are described, including an HCl cleaning process, which allows the formation of much more efficient porous silicon sensors. Selectivity and enhanced sensitivity are developed using electroless metal deposition to form a gold or tin oxide nanostructured framework interacting with the nanoporecoated microporous surface. The ability to monitor sensor response in the presence of external noise sources is increased with the introduction of an FFT filtering technique. These studies present the first detection of CO with a porous silicon sensor as well as a considerable improvement in the sensitivity to $NH_3$. It is suggested that a diffusion based model can be used to parameterize the response of the sensors. These sensors demonstrate the ability to monitor gas mixtures as exemplified by the $NH_3/NO_x$ system. The potential for these sensors in arrayed configurations with integrated CMOS devices is considered.

Utilizing CMOS fabrication methods, a system has been developed to provide cost-effective monitoring of air quality and polluting gas emissions. The fabrication of porous silicon based sensors are described, which, while operating at room temperature, are selective to a wide variety of these polluting gases. Highly sensitive, rapidly responding room temperature devices have been produced based upon a porous silicon interface that is able to repeatedly detect gaseous, HCl, $NH_3$, $SO_2$, CO, $H_2S$, $NO_x$ and gas mixtures.

Fabrication

The PS gas sensors are 5×2 mm in size, so as to allow a much more rapid treatment and handling of the devices during testing. These milli-scale devices represent the majority of sensors which have been tested and will be the primary focus of discussion. We have modified two aspects of the fabrication procedure to produce porous silicon gas sensors to greatly improve the operation of these devices. As well as providing a more consistent fabrication, the process (FIGS. 6A through 6H) improves the sensitivity of the gas sensor from the previously reported design. The previous fabrication process, resulting in low resistance 20 Ω contacts to produce low power devices, has been modified with the process depicted in FIGS. 6A through 6H. The described process has been developed to minimize the contact of water on the PS gas sensors, which was observed to be harmful to device sensitivity (e.g., signal to noise).

Each batch of PS gas sensors is fabricated on the polished surface of a test grade p-type (100) silicon wafer with a 1–20 Ω-cm resistivity. After an initial cleaning of the wafer, a silicon carbide layer is deposited on the polished surface of the device. This carbide layer isolates the formation of porous silicon during the etch process. Next, a photoresist layer (Shipley 1827) is spun onto the carbide and patterned with photolithography. This step defines windows in the photoresist exposing portions of the carbide that are to be removed. An $SF_6$ Reactive Ion Etch process is used to remove the exposed carbide, revealing the underlying silicon. A cleaning process removes the remaining photoresist and yields a silicon wafer with silicon carbide defined windows on its surface.

Creation of the Porous Silicon Layer

To produce a porous silicon film, conductive copper tape is used to create a good electrical contact to the back side of the prepared silicon wafer. The wafer is placed into a high density polyethylene (HDPE) container as a platinum sheet is placed about 5 mm from the wafer's surface. This receptacle contains an etch solution consisting of 1M $H_2O$, 1M HF, and 0.1 M TBAP in acetonitrile. The etch takes place at room temperature over 5 to 30 minutes at a constant current density which can be set between 4 and 8 $mA/cm^2$ and can produce a structure with pores 1 µm wide and 1–20 µcm deep. Following the etch process, the porous structure is rinsed in methanol and allowed to dry under $N_2$.

This specific etching procedure leads to the formation of a hybrid micro/nano-porous layer (macro/nanoporous layer) on the silicon wafer. The sensor utilizes the high surface area and large number of active sites present in this film to facilitate the rapid transduction of analyte gas concentrations. This hybrid porous silicon film also is characterized by tunable photoluminescence (PL) which has been demonstrated to provide a control mechanism to enhance the surface reactivity. The PL, which occurs on the surface of the pores, can be excited by ultraviolet light resulting in the emission of photons in the green to red-orange range of the spectrum. The porous surface is made more chemically active as it is stimulated by UV light yielding a PL emission that results from the presence of electrons in higher energy states within the structure.

Deposition of Metal Contacts

A metal layer is deposited onto the surface of the porous silicon to produce electrical contacts for device testing. Gold is chosen for the contacts since it does not corrode and has a high conductivity. In previously reported fabrications of the sensors, photolithography was used to define the electrodes, which were subsequently deposited through a combination of electroless coating and metal evaportion. Electroless gold can be used to facilitate the formation of low resistance electrical contacts to the porous silicon surface with resistances as low as 20 Ω. The electroless gold deposition utilizes porous silicon PL induced metallization to precipitate gold from the electroless solution at the photo-active sites on the surface of the pores. A conformal coating of gold along the surface of each pore is produced which can be followed by a subsequent deposition of gold via a physical vapor deposition to provide the low contact resistance. These devices require less power to operate than other kΩ resistance sensors which is preferable for portable applications. However, testing on several sensors reveals that the exposure of the porous interface to liquid water present during a photolithography step can irreversibly degrade sensitivity as it produces an amplified noise level in the device. Water is believed to cause damage to the sensors because of the high rate of oxidation of silicon microstructures in its presence. This suggested mechanism for degradation is supported by the observation of similar device degradation upon heating to 90° C. in the presence of atmospheric (20%) oxygen. Heating of devices to the same temperature under a constant flow of research grade nitrogen does not cause device degradation, and the application of methanol, which can be used to remove water from the pores through leaching from the surface, reduces the damage done by water to device sensitivity. Since the photolithographic process both requires the application of water and is intolerant to solvents such as methanol, a new method of forming electrical contact was investigated.

For the process illustrated in FIGS. 6A through 6H, a shadowmask fabricated from copper foil was made to replace the photolithography step so as to produce nine resistive devices and three four-point devices on a given wafer. After the porous silicon etch, the shadow mask was affixed to the surface of the wafer and both were inserted into an electron-beam metal evaporation system. A 200 Å layer of titanium and an 1800 Å layer of gold were deposited to produce the contacts. Twelve individual sensors were scribed from the fabricated wafer.

Figure 10:
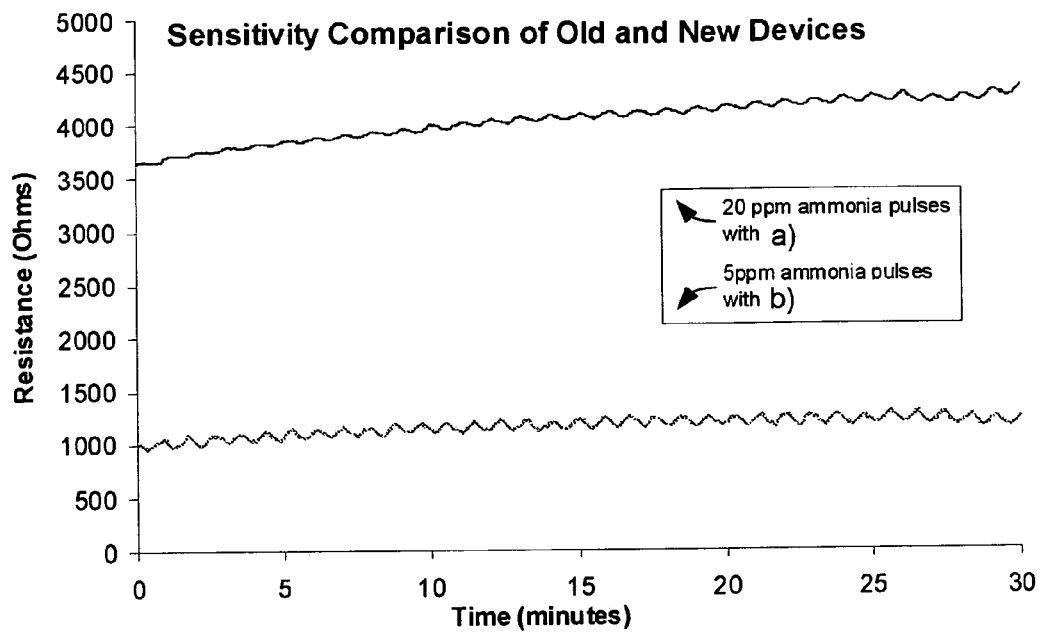
FIG. 10 illustrates sensor responses with contacts created from a) a photolithographic masking procedure and b) a shadowmask masking procedure.

Devices constructed using the shadowmask technique showed a considerable improvement in sensitivity. The improvement in sensitivity gained with the outlined fabrication method is at the expense of higher impedance devices. However, introducing the lower impedance PL induced contacts to other devices, where water is readily removed or not deleterious would appear to be quite feasible. FIG. 10 demonstrates the performance of two sensors. The first device (a) was fabricated using the photolithography; the second device (b) was fabricated using the shadow mask as outlined in FIGS. 6A through 6H, neither used electroless gold metallization to improve contacts. Both sensors were cycled between a concentration of test gas and pure $N_2$ in a "gas pulsing test" (see testing section) of their sensitivity. The quality of the response of the sensor fabricated with process shown in FIGS. 6A through 6H exceeded that of the sensor produced with photolithography at a lower concentration of ammonia.

HCl Cleaning Process

Figure 11:
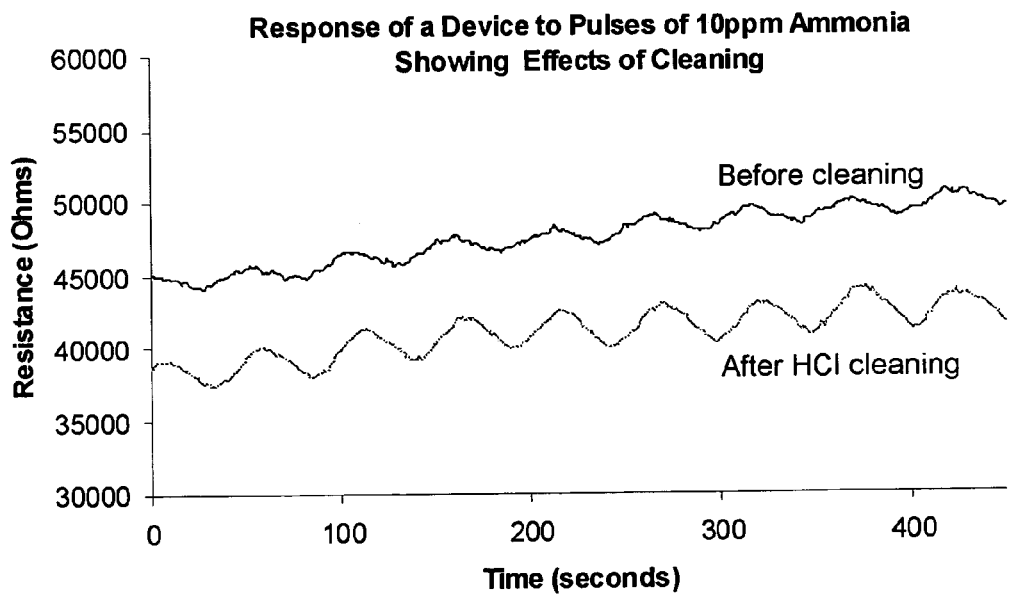
FIG. 11 illustrates the response of a PS film-based sensor before and after cleaning in about a 1:5 HCl in methanol solution at room temperature.

In a series of experiments focused on the characterization of the photoluminescence from porous silicon, it has been demonstrated that the emission can be optimized and stabilized through an HCl cleaning process. The HCl cleaning process appears to further activate the surface of the porous silicon by increasing the density of activated sites. This method of stabilization has been used in part to develop an enhancement of selectivity for the porous silicon sensors. A device is cleaned to maximize the photoluminescence by soaking in 1 (HCl):5(MeOH) 44% HCl in methanol for four hours. The device is then rinsed by immersion in methanol and dried under $N_2$. FIG. 11 demonstrates the notable improvement in the response of a sensor after being cleaned using this process.

Selective Coating Technique

In an effort to enhance the sensitivity and selectivity of the sensor surface by depositing a minimal amount of metal on the sensors, a short exposure electroless metallization procedure was developed and tested. Here, for example, an HCl-cleaned sensor was immersed in a commercially available (Transene) electroless gold metallization solution for 30 seconds. It was then rinsed by brief immersion in DI water, followed by a 30 second rinse in methanol. This device produced a noticeably improved sensitivity to $NH_3$. A second electroless solution containing tin was used to deposit a layer of $SnO_x$. This coating deposited a thin layer of tin during a 20 second immersion which, after a rinse in water and methanol, oxidized to $SnO_x$ and initiated a device sensitivity to 10 ppm CO (which has since been lowered to <5 ppm). The results outlined here mark the first demonstration of a room temperature tin-oxide based CO sensor. In addition tin oxide sensors normally operate at 300–500° C. Within this format, a general approach was established using the electroless deposition of metals to provide selectivity and enhanced sensitivity to the porous silicon gas sensor. The process of determining the most successful method of depositing each new coating and at small enough concentration is distinct for each transformation and desired detection mode.

The changes that are described enable the fabrication of an improved gas sensor. The operation of this new device has been demonstrated, using several different testing procedures, and a sensitivity to a wide range of gases at the low-ppm to ppb level has been shown. It is also demonstrated that this method of applying selective coatings through electroless deposition suggests the feasibility of utilizing this technology to produce arrayed sensors.

Testing

The PS gas sensor is tested within a configuration designed for rapid and easily repeatable experiments. The analyte delivery system provides a continuous flow of research grade nitrogen over the sensor surface at 100 sccm. The flow can be rapidly modulated with pulses of the desired test gas. Mass flow controllers (MFC's) deliver the test gas into the nitrogen stream from calibrated cylinders containing concentrations of 100 and 1000 ppm $NH_3$, CO, HCl, $H_2S$, $SO_2$ and $NO_x$. The flow rate of the test gas is modulated by the controllers, which are calibrated to a maximum error of 1%, as the test gas is delivered into the nitrogen flow. The gases are mixed at a ⅛" junction and then driven onto the surface of the sensor. This configuration allows the devices to be tested between 0.01% and 1% with a 1 sccm mass flow controller delivering the gas from the calibrated cylinder. The pulses of test gas controlled by an MFC are delivered to the sensor with no more than a 2 second delay due to the length of tubing between the MFC and the device.

The sensor is connected to precision microprobes (DCM, Microtech) that are in turn connected to an impedance analyzer (Model 1260, Solatron). In order to transduce the resistance (the real part of the impedance) of the sensor as accurately as possible, impedance sweeps are performed with a generated 100 mV AC drive voltage at 1 kHz. Measurements can likewise be taken with a supply voltage as low as 1 mV AC or by using a 100 mV DC source. All sampling was done at 1 Hz. All of the experiments were conducted at room temperature. However, devices have been demonstrated to withstand temperatures as high as 90° C. for several minutes while returning to normal operation once cooled to room temperature. Two methods for characterizing the porous silicon gas sensors have been developed: a lower exposure limit test and a gas pulsing test. To consider these tests, we first define sensitivity.

Sensitivity

Sensitivity for a given device is defined as the relative increase in impedance over time following exposure to a concentration of sample test gas. During a test, both the resistance and the time are sampled at 1 Hz. To ensure that a sensor platform has recovered from its exposure during previous tests, a flat baseline is established before a test is conducted. Gas is driven to the surface of a sensor for a given period of time, usually between 20 seconds and one minute. As a response is observed, the slope of the response is calculated in Ohms/second. This slope, divided by the value of the resistance before a test gas is delivered to the sensor, is defined as the sensitivity, with units of inverse seconds or Hz.

Figure 12:
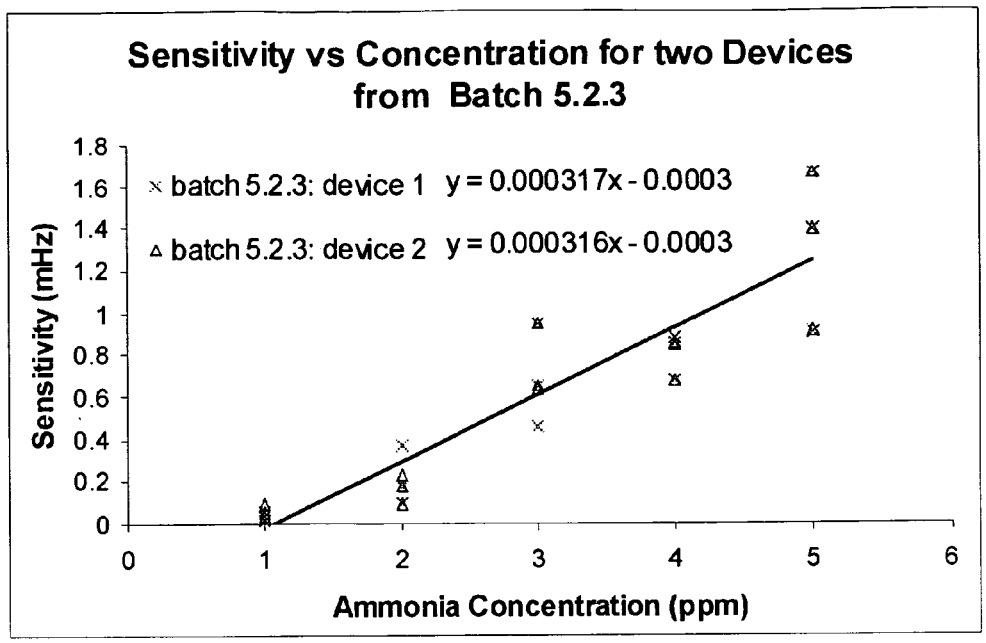
FIG. 12 illustrates that the sensitivity of two devices from a wafer batch (5.2.3) is demonstrated to be nearly the same (slope fit). The sensors tested (devices 1 and 2) had 5 k$\Omega$ and 2 k$\Omega$ baseline resistances, respectively.

This definition of sensitivity is used because the sensors as fabricated vary in impedance from hundreds to thousands of Ohms within a given batch. However, sensors from a given batch show similar sensitivities. Two of the nine resistive devices formed in a particular fabrication run (5.2.3) were subjected to identical tests. FIG. 12 depicts a plot of the calculated sensitivity plotted against the concentration of ammonia tested. Though the baseline impedances of the devices were 5 kΩ and 2 kΩ respectively, their sensitivities were nearly identical. The sensitivity of devices does vary slightly from batch to batch, primarily due to the degree of variation in the parameters controlling the porous silicon etch. However, the ability to confidently determine the sensitivity of an entire batch through testing only a few devices is vital to the practical use of this technology. The devices, though higher in impedance than previous porous silicon gas sensors which we have developed in our laboratory, demonstrate highly repeatable sensitivity with only a small variation for sensors tested from the same wafer.

Lower Exposure Limit Test

Figure 13:
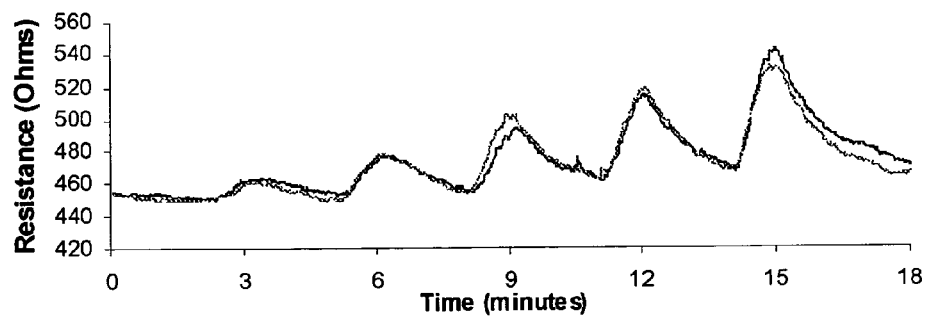
FIG. 13a illustrates the resistance of a sensor exposed to one minute pulses of 1–5 ppm $NH_3$ in $N_2$.
FIG. 13b illustrates a plot of the slopes of the data in FIG. 13a which demonstrates both the linearity and sensitivity of the response.
Figure 13:
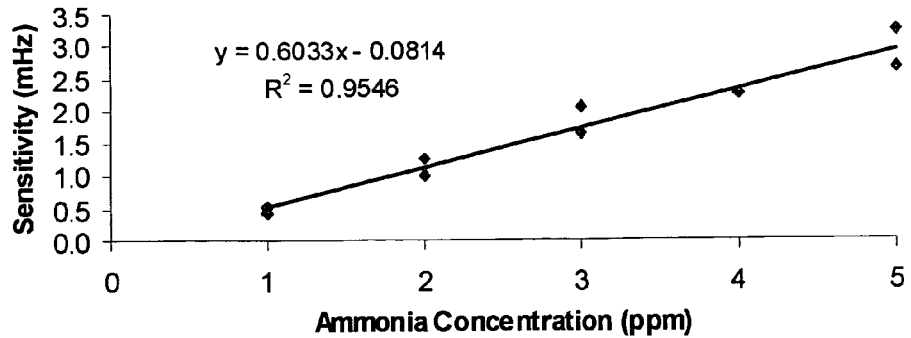

A second test was performed to determine the lower exposure limit (LEL) of a given device, or the lowest concentration of gas that the sensor can reliably detect. In this test, gas is pulsed onto the surface at varying concentrations. The shape of the response, which is typically expected to be linear at low concentration, determines the quality of the sensor as well as its detection limit. FIGS. 13a and 13b demonstrate the performance of a sensor as it detects different levels of ammonia. Repeat tests were conducted on a device exposed to controlled levels (1, 2, 3, 4, 5 ppm) of $NH_3$ with a 1 minute exposure time followed by two minutes with pure research grade $N_2$. FIG. 13b is a plot of the sensitivity of the data presented in FIG. 13a. The sensitivity is plotted with respect to the exposure concentration, which is used to determine the limit of detection for the sensor. The standard deviation for the collected data from the linear fit shown in FIG. 13b is 0.214 mHz. To ascertain the lowest concentration of gas that can be detected with 95% (within two possible standard deviations of the error) confidence, the deviation of the sensitivity from the linear fit of the data is first calculated. The linear fit is solved for the concentration at the point where the sensitivity is twice this deviation, giving the LEL for a sensor. This indicates that, with 95% confidence, the LEL is near 700 ppb for the detection of ammonia with this device. This sensor was untreated with electroless gold, which in other devices has dramatically improved their sensitivity to ammonia (see following). This device was from batch 5.2.2 (which had twice the etch time of batch 5.2.3) and displayed a sensitivity to $NH_3$ approximately twice that of the devices shown in FIG. 12.

Gas Pulsing Test

Figure 14:
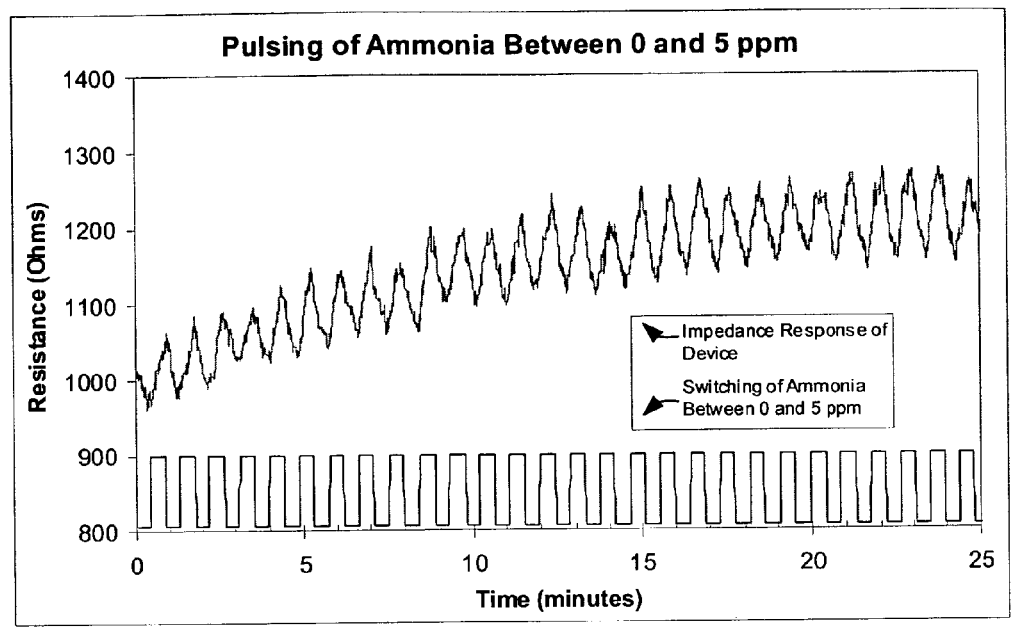
FIG. 14 illustrates a gas sensor response to pulsing of ammonia between 0 and 5 ppm (in research grade nitrogen).

In the gas pulsing test, the flow rate of the test gas is pulsed on and off in a periodic manner. Since the gas sensor responds with an impedance change proportional to the gas concentration, a highly periodic gas signal is produced. The periodicity of this response allows an FFT algorithm to extract, filter, and determine the magnitude of the response, in the presence of noise. FIG. 14 demonstrates both the pulse signal of the gas being delivered, as well as the response of the sensor. The upward drift in this data is from the gradual accumulation of ammonia onto the surface of the sensor. This drift ceases when the adsorption and desorption rates are equilibrated. The primary purpose of this mode of experiment is to evaluate the degree of sensitivity that the sensor has to a given gas.

Figure 15:
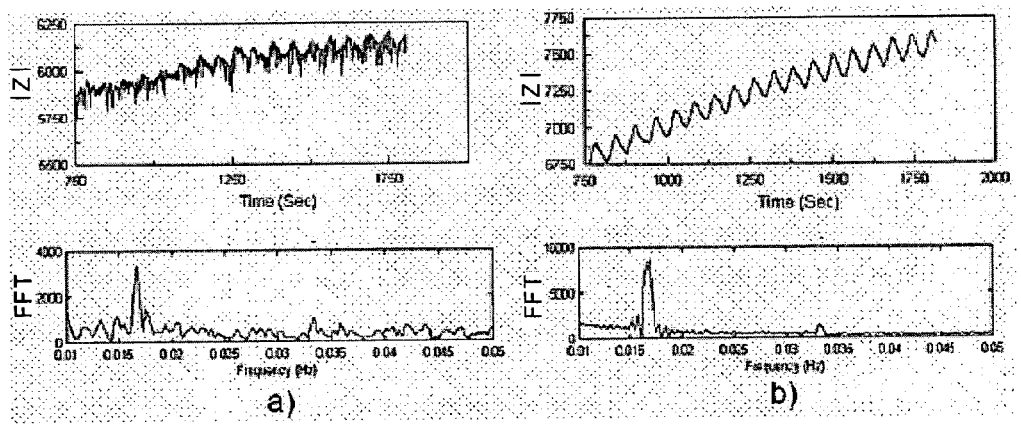
FIG. 15a illustrates a signal and frequency transform for a sensor having a high background, but through using the gas pulsing method and analysis described below the gas signal ($NH_3$ in $N_2$) can be measured.
FIG. 15b illustrates a signal and frequency transform for a PS gas sensor exposed to large concentrations of a gas, but through using the gas pulsing method and analysis described below the gas signal can be measured. The response to a 60 second gas pulsing cycle (0.017 Hz) is clear in both cases.

With the FFT analysis, the signal, background noise, and drift can be systematically separated (see FIGS. 15a and 15b). The response is clearly shown in the FFT at 0.017 Hz regardless of the noise level of the device. By selectively filtering frequencies associated with the noise, a high fidelity gas response can be produced. After ascertaining the validity of the gas sensor response, one can systematically extract the corresponding resistance values. Since higher frequency noise is present, numeric integration is not effective. Rather, using a novel algorithm based upon frequency domain analysis, the impedance response is extracted from the background noise and baseline. This algorithm was verified against carrier gas, nitrogen in most cases, unresponsive sensors, and fictitious test signals, to ensure the validity of the method. As a final verification against saturation and instability, the dynamic response is tracked for convergent behavior. For example, the response of a device exposed to pulses of 10 ppm $NH_3$ should, if pulsed for a long enough time to approach an average resistance, approach a resistance corresponding to saturation in 5 ppm $NH_3$.

Figure 16:
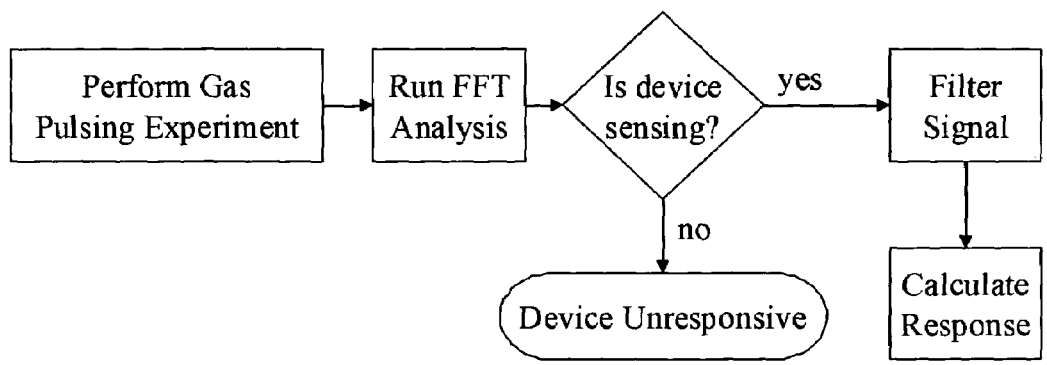
FIG. 16 illustrates a representative flow chart of a data analysis method.

Once implemented, the FFT technique can be used to improve the power requirements to obtain a stable response and reject noise. FIG. 15a illustrates the impedance response (top) (magnitude of the impedance) and FFT signal (bottom) for an electroless gold coated porous silicon gas sensor (previous fabrication method) subjected to 30 pulses of 20 PPM $NH_3$ in $N_2$ at a flow rate of 100 sccm at room temperature powered by a 10 mV (FIG. 15b 150 mv) RMS voltage at 1 kHz AC. The response to a 60 second cycle (0.017 Hz) is clear in both cases. The signal/noise ratio could also be improved significantly with an increased supply voltage. However, even at the lower drive voltage, the sensor response at 0.017 Hz (the gas pulsing frequency) is clearly visible in the FFT. After filtering, the analyte to be detected is determined from the signal amplitude at the gas pulsing frequency with the algorithm summarized in FIG. 16. Note also that the base-line impedance shift over the course of the experiment has no impact on the gas concentration measurements.

This data analysis method for the PS gas sensor offers several safeguards against false positives. The FFT module filters erroneous signals associated with the PS sensor. If the false positive is associated with the delivered gas, attributes of the "time-delay" module become unstable and the dataset is withdrawn.

Sensor Response to Different Gases

Figure 17:
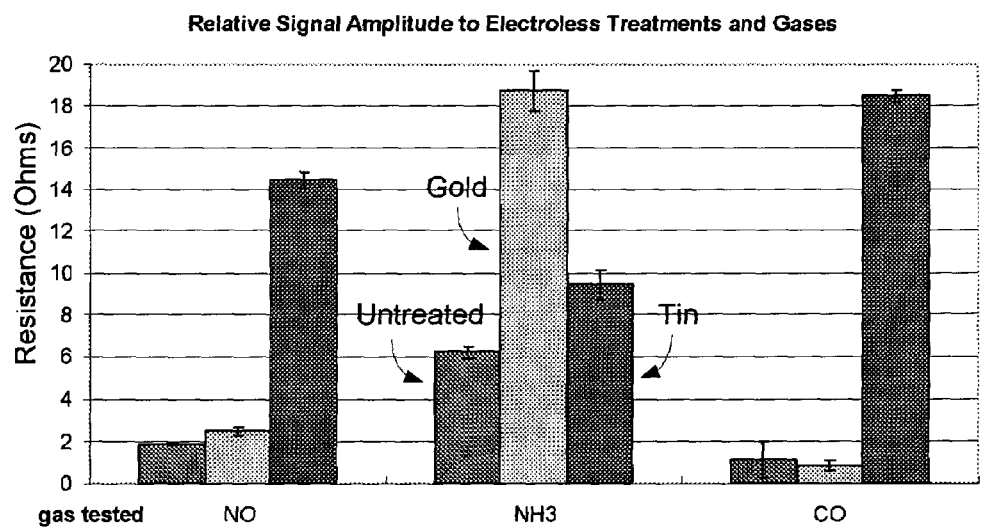
FIG. 17 illustrates a comparison of responses for sensors (prepared by a previous process) that are untreated, treated with electroless gold, or treated with electroless tin, and tested with 30 repeat pulses of 20 ppm $NO_x$, $NH_3$, or CO. Their average resistance change is given.

A substantial number of tests have been performed on devices treated with electroless tin and gold to establish selectivity and the feasibility for creating arrayed selective devices. The tests were conducted for 20 ppm $NO_x$, $NH_3$, and CO using the gas pulsing method. The average response of each coated device to 30 individual pulses of gas was calculated and plotted for each test gas. FIG. 17 demonstrates an exemplary result of this test and indicates a capability to use selectively coated devices as a means of creating arrays to discriminate between $NO_x$, $NH_3$, and CO. For example, if a sensor was needed to detect $NH_3$ in the presence of $NO_x$, FIG. 17 demonstrates such a device could be obtained with an uncoated sensor and a gold coated sensor since the two sensors have a significantly disproportionate response to these gases.

Figure 18:
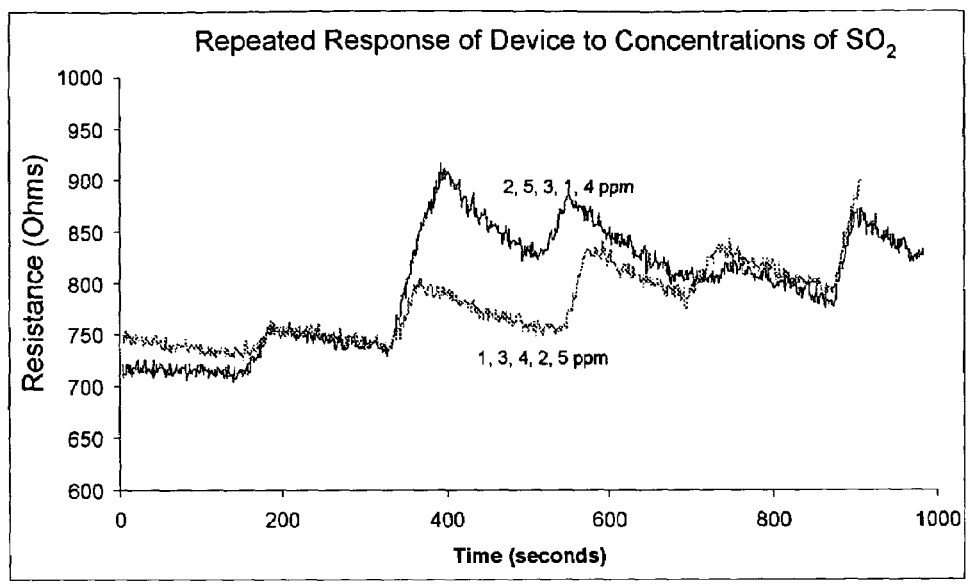
FIG. 18 illustrates a measured resistance for two LEL tests on a device treated with electroless gold and tested with low concentrations of $SO_2$ in $N_2$. The response is similar for the two tests, and can be noted to be in the 1–5 ppm data points for $SO_2$ depicted in FIG. 19.
Figure 19:
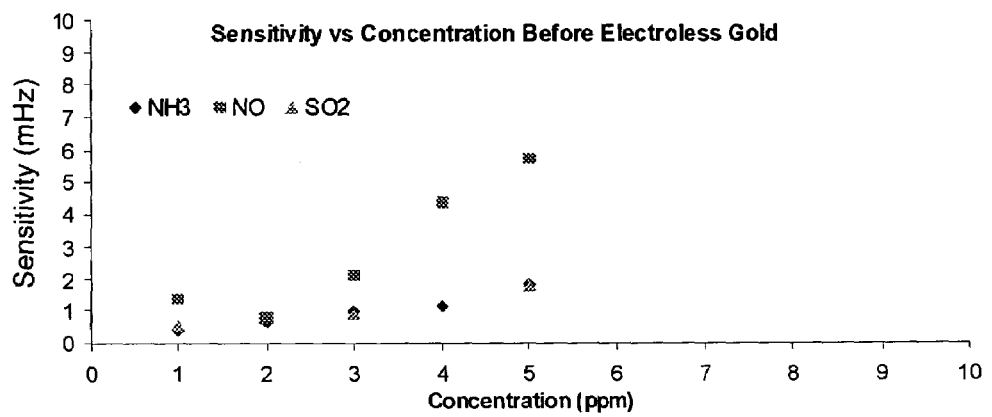
FIG. 19 illustrates graphs of LEL tests for several devices both before and after their treatment with electroless gold. Concentrations vary from 0.5 to 10 ppm of $NH_3$, $NO_x$, and $SO_2$.
Figure 19:
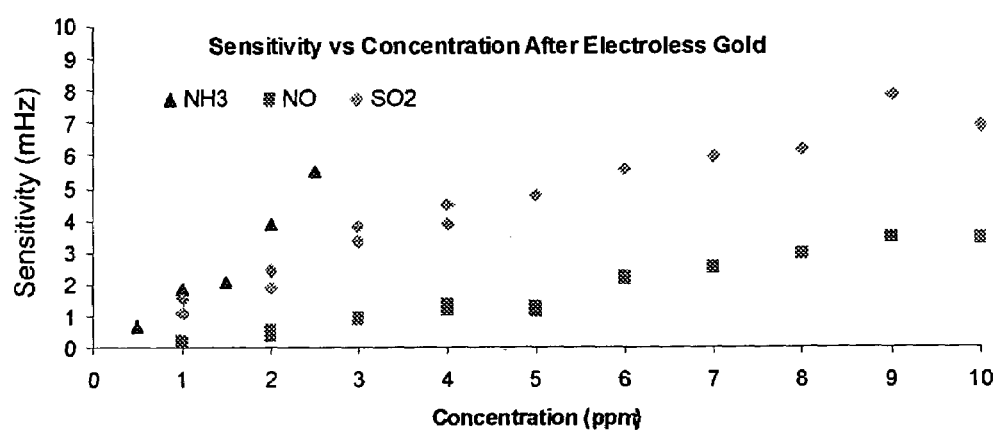

Using a gold coated sensor fabricated with FIGS. 6A through 6G, which is particularly applicable, testing has been performed for a response to $SO_2$. The results for two tests conducted on a device for concentrations of between 1–5 ppm $SO_2$ are plotted in FIG. 18. Further experiments which indicate the nature of the improvement in sensitivity provided to devices by the electroless gold coating technique are summarized in FIG. 19. LEL tests were conducted on devices both before and after treatment with electroless gold with concentrations of $NH_3$, $NO_x$, and $SO_2$ ranging from 1 to 10 ppm. FIG. 19 demonstrates that the $NO_x$ response is reduced in this range in contrast to that at higher concentrations. However, the $SO_2$ and $NH_3$ responses both increase when the porous silicon surface is sensitized with gold.

Suggestion of a Diffusion Based Model

The data generated in evaluating the PS gas sensors has enabled the development of a model to characterize the transient response. By defining sensitivity as the rate of change in resistance divided by the baseline resistance, the transient response is more significant than the steady state resistance value. Using this approach, it was established that the sensitivity is linearly proportional to the concentration of the species of gas to which the sensor is exposed. The behavior was studied by allowing a device to saturate in the presence of several concentrations between 1 and 5 ppm of $NH_3$ and has important implications for the development of viable, integrated sensors. The speed of the response of the porous silicon sensors is in part defined by the rate of diffusion of the analyte gas into the porous structure. We suggest that while Fickian diffusion governs the diffusion into the microporous structure, Knudsen diffusion occurs in the nanopores coating the walls of the micropores. We have examined the diffusion at both scales to determine which process (or combination of processes) best matches with the data. For this analysis, we assume that the reaction rate of the adsorbtion of the gas to the porous silicon film surface occurs at a much shorter timescale than the process of diffusion. As a result, the concentration of the gas inside the pore $C(x,t)$ is proportional to the adsorbed species of gas.

As a first step to describe diffusion into the sensor, we approximate the porous silicon device as a collection of one dimensional semi-infinite wells with a constant concentration of gas present at the open end. The equation governing diffusion for each of these wells is given by Fick's law as shown in Equation 1:

$$\frac{dC(x,t)}{dt} = D_{ps}\frac{d^2 C(x,t)}{dx^2} \quad (1)$$

where $D_{ps}$ is the diffusion constant for the gas in porous silicon. The boundary conditions for this equation, given diffusion into a pore of finite depth from an infinite source are listed in Equation 2:

$$C(x,t)|_{t=0} = 0 \quad C(x,t)|_{x=0} = C_0 \quad \left.\frac{dC(x,t)}{dt}\right|_{x=L} = 0 \quad (2)$$

where $C_0$ is the concentration of gas at the surface of the sensor. Evidence suggests that electrical conduction through porous silicon occurs predominantly at the porous silicon—silicon interface. This is supported by the observation that electrolessly deposited conformal coatings establish contact to porous silicon devices at the interior of the porous structure, whereas higher resistance devices result from the use of only the physical vapor deposition of contacts at the surface of the pores. Therefore, an exponential decay function is used to describe the decay of the response away from the bottom of the pores. Given this surmise, the suggested response of a device to a gas species 'i' is given by Equation 3.

$$\Omega_i(t) = \Omega_0 + S_i \int_0^L C(x,t)\frac{Be^{Bx}}{1-e^{BL}}dx \quad (3)$$

The constants represented within this equation are established rigorously through experiment. $\Omega_0$ is the baseline resistance and includes both the resistance of contact formation to the sensor as well as the resistance of the pores under dry $N_2$. $S_i$ is the impedance response of the device per concentration of gas species i. This is established by saturating the device and measuring the total impedance change. L is the pore depth, which can be controlled by varying the time of the etch process. The quantity B, given in units of 0.4 μm, which characterizes the preference for conduction closer to the bottom of the pores, is left as a variable quantity at this time. It can be fitted in the model through calculation of the initial rate of increase in resistance of the sensor. Future tests of devices with varying pore sizes will establish these quantities more precisely.

Figure 20:
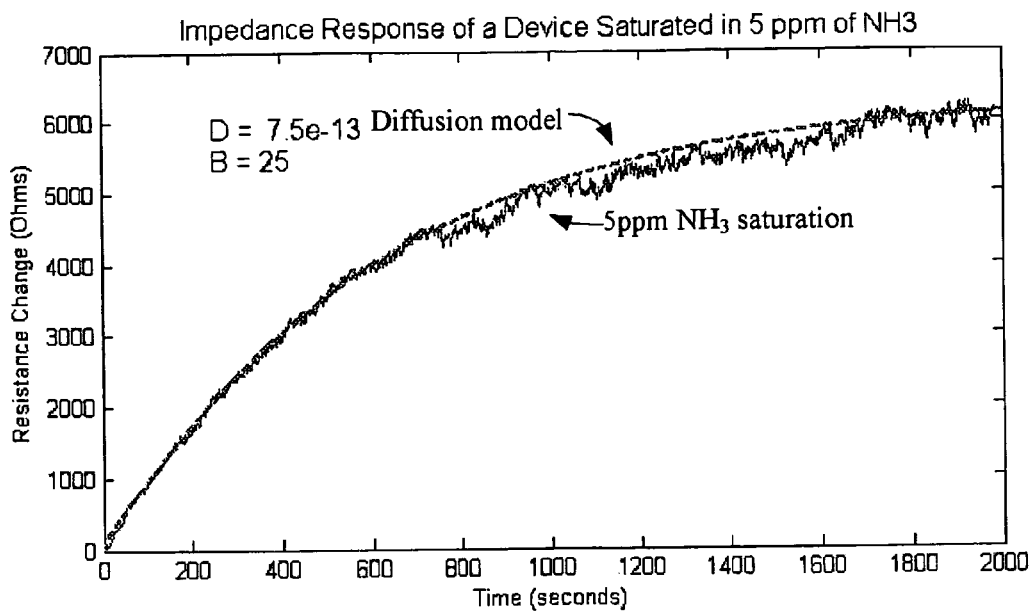
FIG. 20 illustrates the response of a device (with baseline removed) under 5 ppm $NH_3$ saturation and the value of the impedance change as given by the diffusion model discussed in the text.

By saturating a sensor in 5 ppm $NH_3$ over 30 minutes, we evaluated the ability of the Equation 3 to model the device performance. FIG. 20 depicts both the response of the device, and the fitted model for the data. The correlation indicated in this figure suggests two factors. First, the sensor response appears to be driven by Knudsen diffusion, potentially within pores of sub-nanometer size containing rough walls. This is suggested since the diffusion coefficient is of such a low order of magnitude. Contrasting the fitted diffusion coefficient of 7.5e-13 $m^2/s$, open air diffusion of $NH_3$ in Air is 2.8e-4 $m^2/s$, and Knudsen diffusion within a smooth pore of nanometer size is on the order of 1 e-7 $m^2/s$. Second, the response appears to be transduced at chemically active sites located at the nanoporous sites present at the walls and at the bottom of the pores.

Operation in a Mixed Gas Format

Figure 21:
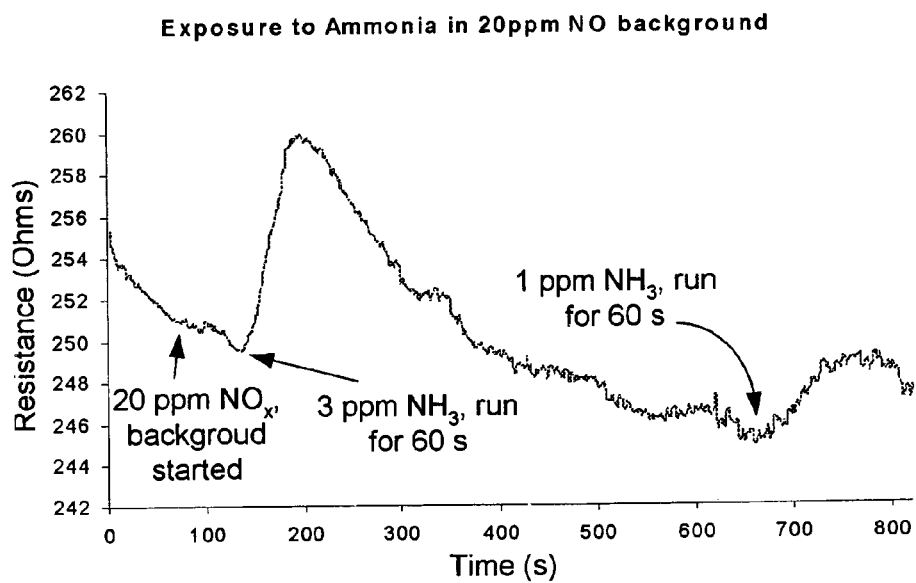
FIG. 21 illustrates the selectivity of a porous silicon device to pulses of 3 ppm and 1 ppm $NH_3$ in the presence of 20 ppm $NO_x$. The fast response time (<10 seconds) of the gas sensor is also demonstrated.

As an inexpensive means to determine soil quality levels in the presence of vehicle exhaust it is appropriate to develop a device to measure $NH_3$ levels in the presence of an $NO_x$ background. In order to approach this need we have now demonstrated a device that has this functionality. FIG. 21 demonstrates a relative insensitivity to 20 ppm $NO_x$, while also responding to 1 ppm of $NH_3$ without gold coatings. For soil quality evaluation, ammonia detection is needed in the 5 to 20 ppm range. A second similar application would also be the monitoring of ammonia in establishing food quality. The 1 ppm detection level needed for this application is easily accessible with the current sensors.

SUMMARY AND CONCLUSION

Modifications made in the fabrication of porous silicon sensors have resulted in the creation of much more sensitive and reversible gas sensors than previously reported. Whereas previous device fabrications provided less than a 20% yield of effective gas sensors, 100% of all the devices now fabricated are demonstrated to provide a working format for selective sensing. The previously reported devices displayed a detection limit of 7 ppm for $NH_3$ and 7 ppm for $NO_x$. In contrast, the current devices fabricated with the process illustrated in FIGS. 6A through 6H responds to 700 ppb of $NH_3$, and below 5 ppm of CO and $NO_x$. The higher yield of devices with improved sensitivity and stability results from (1) the implementation of computer controlled etching, (2) the use of a shadowmask, and (3) the use of an HCl cleaning process.

New testing procedures allow better characterization of the gas sensors. Two distinct methods are reported to establish the sensitivity and selectivity of these conductometric devices. These methods have also allowed the suggestion of a model for the mechanism of response that can be utilized to tune the structure of the porous silicon to enhance sensitivity and provide selectivity. The testing methods are augmented by an FFT algorithm that is implemented to enhance the fidelity of the sensor.

Several potential applications can be envisioned for the current sensor platform. These applications will require sensitive and selective devices, as well as demonstrate reliability under a range of operating conditions. The conductometric gas sensors discussed here are of primary interest due to their simplicity of operation, low cost of fabrication, and ease of operation. Several potential applications for the PS gas sensor which are among the more motivating are considered in Table 1. The most obvious use for these gas sensors would be for the monitoring of air quality as long term exposure to levels of 25 ppm $NH_3$, 30 ppm CO, and 5 ppm NO are harmful to personal health. However, multifarious additional applications are possible.

TABLE 1

A sampling of gases which can be considered for testing and their potential application.

| Gas | LEL | Industry |
|---|---|---|
| Ammonia | 800 ppb | Agriculture |
| Ammonia | 25 ppm | Health & Air Quality |
| Carbon Dioxide | .5% | Air Quality |
| Carbon Monoxide | 50 ppm | Automotive Emissions/Health & Air Quality |
| Carbon Monoxide | 10 ppm | Fuel Cells |
| Hydrogen | 0.05% | ONR/Fuel cells/Hydrogen Economy |
| Hydrogen Sulfide | 20 ppm | Fuel cells/Health & Air Quality |
| Hydrocarbons | 500 ppm | Air Quality |
| Nitric Oxide | 20 ppm | Agriculture/Automotive Emissions |
| Ozone | 0.1 ppm | Air Quality |
| Sulfur Dioxide | 5 ppm | Fuel cells/Air Quality |

Another potential application of these conductometric devices would be to test both cabin air quality and emissions in automobiles. While carbon monoxide is of primary interest, $NO_x$, hydrocarbons, and sulfurous gases can also be monitored for a fully functional sensor platform at the low ppm level. The implementation of selective metal coatings has been demonstrated to provide the functionality required for this application. Fuel Cells powered by hydrogen or methanol are rapidly becoming of major interest to the world economy. Sensors capable of determining the content of CO, sulfurous compounds, and hydrogen levels are needed to operate a fuel cell successfully. Personal air quality measuring devices for hazardous work conditions are yet another potential application for such a cost-effective sensor. Finally, military and homeland security applications abound for an inexpensive system that can detect trace levels of harmful gases.

The PS gas sensor has been demonstrated to be a platform for stable, reversible, and inexpensive detection of several gases. The devices continue to work months after their initial fabrication without requiring cleaning or recalibration. The two-mask fabrication process allows the devices to be created quickly. In addition, the sensors are compatible with CMOS technology, allowing for an eventual integration with Lab-on-chip technologies to provide a low-cost and low-power portable array based platform to test air quality.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

The invention claimed is:

1. A device, comprising:
a conductometric porous silicon gas sensor including a monolithic silicon substrate having a porous silicon layer and a protective layer, wherein the protective layer is disposed on top of the silicon substrate and adjacent to the porous silicon layer, wherein the protective layer is selected from a silicon carbide layer, a silicon nitride layer, a polymer layer, a silicon oxynitride layer, an insulating dielectric film, a ceramic layer, a photoresist layer, a polyimide layer, and combinations thereof,
wherein the porous silicon layer has a first portion and a second portion that are not contiguous,
wherein the protective layer has a first portion and a second portion that are not contiguous, wherein the first portion of the protective layer is contiguous with the first portion of the porous silicon layer, wherein the second portion of the protective layer is contiguous with the second portion of the porous silicon layer,
wherein a first metal layer is disposed on the first portion of the porous silicon layer and the first portion of the protective layer to form a first contact,
wherein a second metal layer is disposed on the second portion of the porous silicon layer and the second portion of the protective layer to form a second contact, and
wherein the conductometric porous silicon gas sensor is operative to transduce the presence of a gas into an impedance change across the first contact and the second contact, wherein the impedance change correlates to the gas concentration.

2. The device of claim 1, wherein the conductometric porous silicon gas sensor is operative to measure the impedance change corresponding to a gas concentration of 1 part per billion and greater.

3. The device of claim 1, wherein the conductometric porous silicon gas sensor is operative to measure the impedance change corresponding to a gas concentration in at least 2 seconds.

4. The device of claim 1, wherein the impedance change is measured with an impedance analyzer.

5. The device of claim 1, wherein the impedance change is measured with a sensor and shunt circuit.

6. The device of claim 1, wherein the gas concentration is correlated with a change in the magnitude of the impedance or resistance.

7. The device of claim 1, wherein the gas is selected from $H_2S$, HCl, $SO_2$, $NH_3$, and nitric oxide.

8. The device of claim 1, wherein the conductometric porous silicon gas sensor is operative to measure the impedance change corresponding to at least one of the following: a gas concentration of HCl at 1 part per million and greater, a gas concentration of $H_2S$ at 1 part per million and greater, a gas concentration of $SO_2$ at 1 part per million and greater, a gas concentration of $NH_3$ at 0.4 part per million and greater, a gas concentration of nitric oxide at 1 part per million and greater, and combinations thereof.

9. The device of claim 1, wherein the conductometric porous silicon gas sensor is operative to measure the impedance change corresponding to at least one of the following: a gas concentration of HCl at 1 part per billion and greater, a gas concentration of $H_2S$ at 1 part per billion and greater, a gas concentration of $SO_2$ at 1 part per billion and greater, a gas concentration of $NH_3$ at 1 part per billion and greater, a gas concentration of nitric oxide at 1 part per billion and greater, and combinations thereof.

10. The device of claim 1, wherein the first metal layer and the second metal layer each comprise a metal selected from titanium, gold, and combinations thereof.

11. The device of claim 1, wherein the conductometric porous silicon gas sensor is operative to transduce the presence of the gas into an impedance change across the first contact and the second contact at room temperature.

12. The device of claim 1, further comprising a coating layer disposed on a third portion of the porous silicon layer that is between the first portion and the second portion of the porous silicon layer.

13. The device of claim 12, wherein the coating layer is selected from tin, gold, and combinations thereof.

14. The device of claim 12, wherein the coating layer is selected from the following: tin oxides, gold clustered oxides, and combinations thereof.

15. The device of claim 12, wherein the coating layer is selected from the following: platinum, oxides thereof, and oxynitrides thereof palladium, oxides thereof, and oxynitrides thereof; iridium, oxides thereof, and oxynitrides thereof rhodium, oxides thereof, and oxynitrides thereof; vanadium, oxides thereof, and oxynitrides thereof ruthenium, oxides thereof, and oxynitrides thereof; titanium, titanium oxide, and titanitum oxynitride; tin oxynitride; and combinations thereof.

16. The device of claim 12, wherein the conductometric porous silicon gas sensor is operative to measure the impedance change corresponding to a gas concentration at 400 parts per billion and greater.

17. The device of claim 12, wherein the conductometric porous silicon gas sensor is operative to measure the impedance change corresponding to a gas concentration at 1 part per billion and greater.

18. The device of claim 12, wherein the conductometric porous silicon gas sensor is operative to measure the impedance change corresponding to a gas concentration of CO at 5 parts per million and greater.

19. The device of claim 12, wherein the conductometric porous silicon gas sensor is operative to measure the impedance change corresponding to a gas concentration of CO at 1 part per billion and greater.

20. The device of claim 12, wherein the conductometric porous silicon gas sensor is operative to measure the impedance change corresponding to a gas concentration of $NH_3$ at 1 part per million and greater in the presence of nitric oxide at 20 parts per million and less.

21. The device of claim 1, wherein the porous silicon layer has a hybrid microporous/nanoporous framework, wherein the walls of the microporous framework are superimposed with a nanoporous layer.

22. The device of claim 21, wherein the macroporous framework includes pores approximately 1 to 2 μm wide and 0.5 to 20 μm deep.

23. A device, comprising:

a conductometric porous silicon gas sensor including a monolithic silicon substrate having a porous silicon layer and a protective layer;

a first contact disposed on a first portion of the porous silicon layer and a first portion of the protective layer; and a second contact disposed on a second portion of the porous silicon layer and a second portion of the protective layer, wherein the conductometric porous silicon gas sensor is operative to transduce the presence of a gas into an impedance change across the first contact and the second contact, wherein the impedance change correlates to the gas concentration.

24. The device of claim 23, wherein the conductometric porous silicon gas sensor is operative to measure the impedance change corresponding to a gas concentration of 1 part per billion and greater.

25. The device of claim 23, wherein the conductometric porous silicon gas sensor is operative to measure the impedance change corresponding to a gas concentration in at least 2 seconds.

26. The device of claim 23, further comprising a coating layer disposed on a third portion of the porous silicon layer that is between the first portion and the second portion of the porous silicon layer.

27. The device of claim 26, wherein the coating layer is selected from tin, gold, and combinations thereof.

28. The device of claim 26, wherein the coating layer is selected from the following: tin oxides, gold clustered oxides, and combinations thereof.

29. The device of claim 26, wherein the coating layer is selected from the following: platinum, oxides thereof, and oxynitrides thereof; palladium, oxides thereof, and oxynitrides thereof; iridium, oxides thereof, and oxynitrides thereof rhodium, oxides thereof, and oxynitrides thereof vanadium, oxides thereof, and oxynitrides thereof ruthenium, oxides thereof, and oxynitrides thereof; titanium, titanium oxide, and titanitum oxynitride; tin oxynitride; and combinations thereof.

* * * * *

UNITED STATES PATENT AND TRADEMARK OFFICE
CERTIFICATE OF CORRECTION

| | | |
|---|---|---|
| PATENT NO. | : 7,141,859 B2 | Page 1 of 1 |
| APPLICATION NO. | : 11/094584 | |
| DATED | : November 28, 2006 | |
| INVENTOR(S) | : John DeBoer et al. | |

It is certified that error appears in the above-identified patent and that said Letters Patent is hereby corrected as shown below:

Column 10, line 14, replace "are," with --are--
Column 25, line 32, replace "modulation The PS gas sensor of the" and replace with --modulation. The PS gas sensor of the--

Col. 47, beginning on line 10, delete Claim 15 and replace with the following,
--15. The device of claim 12, wherein the coating layer is selected from the following: platinum, oxides thereof, and oxynitrides thereof; palladium, oxides thereof, and oxynitrides thereof; iridium, oxides thereof, and oxynitrides thereof; rhodium, oxides thereof, and oxynitrides thereof; vanadium, oxides thereof, and oxynitrides thereof; ruthenium, oxides thereof, and oxynitrides thereof; titanium, titanium oxide, and titanium oxynitride; tin oxynitride; and combinations thereof.--

Col. 48, beginning on line 36, delete Claim 29 and replace with the following,
--29. The device of claim 26, wherein the coating layer is selected from the following: platinum, oxides thereof, and oxynitrides thereof; palladium, oxides thereof, and oxynitrides thereof; iridium, oxides thereof, and oxynitrides thereof; rhodium oxides thereof, and oxynitrides thereof; vanadium, oxides thereof, and oxynitrides thereof; ruthenium, oxides thereof, and oxynitrides thereof; titanium, titanium oxides, and titanium oxynitride; tin oxynitride; and combinations thereof.--

Signed and Sealed this

Twenty-first Day of August, 2007

JON W. DUDAS
*Director of the United States Patent and Trademark Office*